(12) United States Patent
Garcia-Bengochea et al.

(10) Patent No.: US 11,844,505 B2
(45) Date of Patent: Dec. 19, 2023

(54) RETRACTOR EXTENSION CLIP SYSTEMS AND METHODS

(71) Applicant: JGMG BENGOCHEA, LLC, Jacksonville, FL (US)

(72) Inventors: Javier Garcia-Bengochea, Jacksonville, FL (US); Marc Von Amsberg, Waxhaw, NC (US); John Souza, Sr., Monroe, NC (US)

(73) Assignee: JGMG BENGOCHEA, LLC, Jacksonville, FL (US)

( * ) Notice: Subject to any disclaimer, the term of this patent is extended or adjusted under 35 U.S.C. 154(b) by 357 days.

(21) Appl. No.: 17/157,287

(22) Filed: Jan. 25, 2021

(65) Prior Publication Data
US 2021/0137511 A1    May 13, 2021

Related U.S. Application Data

(63) Continuation of application No. 16/221,421, filed on Dec. 14, 2018, now Pat. No. 10,898,175, which is a continuation-in-part of application No. PCT/US2018/019029, filed on Feb. 21, 2018.

(60) Provisional application No. 62/598,876, filed on Dec. 14, 2017, provisional application No. 62/461,709, filed on Feb. 21, 2017.

(51) Int. Cl.
*A61B 17/02* (2006.01)
*A61B 17/00* (2006.01)

(52) U.S. Cl.
CPC .......... *A61B 17/0206* (2013.01); *A61B 17/02* (2013.01); *A61B 17/0293* (2013.01); *A61B 2017/00477* (2013.01); *A61B 2017/0256* (2013.01); *A61B 2217/005* (2013.01); *A61B 2217/007* (2013.01)

(58) Field of Classification Search
CPC . A61B 17/02; A61B 17/0206; A61B 17/0218; A61B 17/0293
See application file for complete search history.

(56) References Cited

U.S. PATENT DOCUMENTS

| 1,993,691 A | 3/1935 | Summers |
| 2,347,049 A | 4/1944 | Green |

(Continued)

FOREIGN PATENT DOCUMENTS

| RU | 2440790 C1 | 1/2012 |
| RU | 2373870 C1 | 11/2016 |
| WO | 9320741 A1 | 10/1993 |

OTHER PUBLICATIONS

Search Report issued to PCT counterpart application No. PCT/US2018/019029 by the International Searching Authority dated Jun. 21, 2018.

(Continued)

*Primary Examiner* — Eduardo C Robert
*Assistant Examiner* — Michelle C Eckman
(74) *Attorney, Agent, or Firm* — McNees Wallace & Nurick LLC

(57) ABSTRACT

A retractor extension clip deployment system for use with a surgical retractor includes at least an extension clip adapted for engagement with the surgical retractor, the extension clip having proximal and distal ends, a deployment instrument, and a fluid transport assembly adapted to be affixed to the surgical retractor and comprising one or more tubes for transporting fluid including smoke removal.

20 Claims, 16 Drawing Sheets

(56) References Cited

U.S. PATENT DOCUMENTS

| | | |
|---|---|---|
| 2,632,217 A | 3/1953 | Flora |
| 3,050,066 A | 8/1962 | Koehn |
| 3,998,217 A | 12/1976 | Trumbull et al. |
| 4,190,042 A | 2/1980 | Sinnreich |
| 4,578,060 A | 3/1986 | Huck et al. |
| 4,616,635 A | 10/1986 | Caspar et al. |
| 5,195,506 A | 3/1993 | Hulfish |
| 5,293,863 A | 3/1994 | Zhu et al. |
| 5,353,784 A | 10/1994 | Nady-Mohamed |
| 5,448,990 A | 9/1995 | De Faria-Correa |
| 5,520,610 A | 5/1996 | Giglio et al. |
| 5,620,458 A | 4/1997 | Green et al. |
| 5,656,012 A | 8/1997 | Sienkiewicz |
| 5,792,044 A | 8/1998 | Foley et al. |
| 5,843,097 A | 12/1998 | Mayenberger et al. |
| 5,895,353 A | 4/1999 | Lunsford et al. |
| 5,902,231 A | 5/1999 | Foley et al. |
| 5,928,139 A | 7/1999 | Koros et al. |
| 5,938,680 A | 8/1999 | Ginn |
| 5,954,635 A | 9/1999 | Foley et al. |
| 5,967,973 A | 10/1999 | Sherts et al. |
| 6,083,154 A | 7/2000 | Liu et al. |
| 6,139,493 A | 10/2000 | Koros et al. |
| 6,152,871 A | 11/2000 | Foley et al. |
| 6,159,179 A | 12/2000 | Simonson |
| 6,162,170 A | 12/2000 | Foley et al. |
| 6,206,822 B1 | 3/2001 | Foley et al. |
| 6,206,828 B1 | 3/2001 | Wright |
| 6,210,325 B1 | 4/2001 | Bartie et al. |
| 6,217,509 B1 | 4/2001 | Foley et al. |
| 6,296,609 B1 | 10/2001 | Brau |
| 6,364,833 B1 | 4/2002 | Valerio et al. |
| 6,416,469 B1 | 7/2002 | Phung et al. |
| 6,425,859 B1 | 7/2002 | Foley et al. |
| 6,440,064 B1 | 8/2002 | Rehm |
| 6,464,634 B1 | 10/2002 | Fraser |
| 6,520,907 B1 | 2/2003 | Foley et al. |
| 6,572,541 B1 | 6/2003 | Petersvik |
| 6,575,899 B1 | 6/2003 | Foley et al. |
| 6,592,604 B2 | 7/2003 | Hess et al. |
| 6,679,833 B2 | 1/2004 | Smith et al. |
| 6,716,218 B2 | 4/2004 | Holmes et al. |
| 7,048,744 B2 | 5/2006 | Wiess |
| 7,582,058 B1 | 9/2009 | Miles et al. |
| 7,758,501 B2 | 7/2010 | Frasier et al. |
| 7,774,905 B2 | 8/2010 | Geiger |
| 7,981,031 B2 | 7/2011 | Frasier et al. |
| 8,048,109 B2 | 11/2011 | Garcia-Bengochea |
| 8,771,181 B2 | 7/2014 | Garcia-Bengochea |
| 9,044,280 B1 | 6/2015 | Arambula et al. |
| 9,380,932 B1 | 7/2016 | Lynn et al. |
| 9,636,096 B1 | 5/2017 | Heaton et al. |
| 9,655,505 B1 | 5/2017 | Gharib et al. |
| 9,795,367 B1* | 10/2017 | Lee .................. A61B 1/32 |
| 10,524,831 B2 | 1/2020 | Mather et al. |
| 10,813,692 B2 | 10/2020 | Brannan et al. |
| 2002/0026101 A1 | 2/2002 | Bookwalter et al. |
| 2002/0193809 A1 | 12/2002 | Meade et al. |
| 2003/0013941 A1 | 1/2003 | Cohn et al. |
| 2003/0083688 A1 | 5/2003 | Simonson |
| 2003/0225416 A1 | 12/2003 | Bonvallet et al. |
| 2004/0039397 A1 | 2/2004 | Weber et al. |
| 2004/0087833 A1 | 5/2004 | Bauer et al. |
| 2004/0122293 A1 | 6/2004 | Douglas et al. |
| 2004/0143169 A1 | 7/2004 | Branch et al. |
| 2004/0186346 A1* | 9/2004 | Smith .................. A61M 29/00 600/102 |
| 2005/0080320 A1 | 4/2005 | Lee et al. |
| 2005/0137461 A1* | 6/2005 | Marchek .............. A61B 17/025 600/220 |
| 2005/0149035 A1 | 7/2005 | Pimenta et al. |
| 2006/0030858 A1 | 2/2006 | Simonson et al. |
| 2006/0069315 A1 | 3/2006 | Miles et al. |
| 2006/0200186 A1 | 9/2006 | Marchek et al. |
| 2006/0287584 A1 | 12/2006 | Garcia-Bengochea |
| 2007/0038033 A1 | 2/2007 | Jones et al. |
| 2007/0100212 A1* | 5/2007 | Pimenta ................ A61F 2/4455 600/210 |
| 2007/0208227 A1 | 9/2007 | Smith et al. |
| 2007/0208228 A1 | 9/2007 | Pavento et al. |
| 2007/0260257 A1 | 11/2007 | Phan |
| 2008/0021285 A1 | 1/2008 | Drzyzga et al. |
| 2008/0058606 A1 | 3/2008 | Miles et al. |
| 2008/0183046 A1 | 7/2008 | Boucher et al. |
| 2008/0188718 A1 | 8/2008 | Spitler et al. |
| 2008/0200767 A1 | 8/2008 | Ewers et al. |
| 2008/0319432 A1 | 12/2008 | Ely et al. |
| 2009/0143807 A1 | 6/2009 | Sand |
| 2009/0287061 A1 | 11/2009 | Feigenbaum et al. |
| 2010/0022845 A1 | 1/2010 | Ott et al. |
| 2010/0105985 A1* | 4/2010 | Garcia-Bengochea ...................... A61B 17/02 600/210 |
| 2011/0028792 A1 | 2/2011 | Ibrahim et al. |
| 2011/0301423 A1 | 12/2011 | Koros et al. |
| 2012/0245431 A1 | 9/2012 | Baudouin et al. |
| 2012/0283521 A1* | 11/2012 | Smith ................ A61B 17/0206 600/210 |
| 2013/0102850 A1* | 4/2013 | Fiorella .................... A61B 1/32 600/210 |
| 2013/0178709 A1 | 7/2013 | Suh et al. |
| 2013/0190575 A1 | 7/2013 | Mast et al. |
| 2013/0289354 A1 | 10/2013 | Ainsworth et al. |
| 2014/0135584 A1 | 5/2014 | Lee et al. |
| 2014/0257039 A1 | 9/2014 | Feldman |
| 2014/0330086 A1 | 11/2014 | Mire et al. |
| 2015/0094533 A1 | 4/2015 | Kleiner et al. |
| 2015/0351738 A1 | 12/2015 | Perrow |
| 2016/0015374 A1 | 1/2016 | Gifford et al. |
| 2016/0058494 A1 | 3/2016 | Vayser et al. |
| 2016/0331364 A1 | 11/2016 | Nakajima et al. |
| 2017/0027555 A1 | 2/2017 | Paumier et al. |
| 2017/0119363 A1 | 5/2017 | Nguyen et al. |
| 2017/0333023 A1 | 11/2017 | Adams |
| 2018/0317902 A1 | 11/2018 | Green et al. |
| 2018/0333061 A1 | 11/2018 | Pracyk et al. |
| 2019/0015089 A1 | 1/2019 | Rosenbaum et al. |
| 2019/0183476 A1 | 6/2019 | Garcia-Bengochea et al. |
| 2019/0254650 A1 | 8/2019 | Martinelli et al. |
| 2019/0254702 A1 | 8/2019 | Corbin et al. |
| 2019/0254703 A1 | 8/2019 | Ciampini et al. |
| 2019/0262512 A1 | 8/2019 | Palushi et al. |
| 2019/0321022 A1 | 10/2019 | Karpowicz et al. |

OTHER PUBLICATIONS

International Preliminary Report on Patentability issued to PCT counterpart application No. PCT/US2018/019029 by the International Searching Authority dated Aug. 27, 2019.

* cited by examiner

RETRACTOR EXTENSION CLIP SYSTEMS AND METHODS

RELATED APPLICATIONS

This application is a continuation of and claims priority to U.S. patent application Ser. No. 16/221,421 filed on Dec. 14, 2018, which claims the benefit under 35 U.S.C. § 119(e) to U.S. Provisional Application Ser. No. 62/598,876 filed Dec. 14, 2017, and which is a continuation in part of and claims priority to PCT/US2018/019029 filed Feb. 21, 2018 which claims the benefit under 35 U.S.C. § 119(e) to U.S. Provisional Application Ser. No. 62/461,709 filed Feb. 21, 2017, the entireties of which are incorporated herein by reference.

FIELD

The present application describes various exemplary instruments, systems and surgical techniques for achieving access to and placement of implants at a site within the body, particularly the spine. More particularly, the present application describes instruments and assemblies useful for accessing the spine for one or more purposes of tissue manipulation, and placement of intervertebral implants to supplement or replace natural spinal discs.

DESCRIPTION OF THE RELATED ART

This invention relates generally to the field of devices utilized in surgery to retract and retain tissue, organs or the like to provide the surgeon with access or an unobstructed pathway to an organ, bone, tissue or point in the body. Such devices are typically referred to generically as retractors. More particularly, the invention relates to retractors utilized with minimally invasive surgical techniques, wherein minimally sized openings are created in the body rather than relatively large incisions. Tubular devices known as cannula retractors, or spreading retractors having finger-like extensions or blades, are inserted into the small opening and through or around the body tissues, muscles, tendons, ligaments, etc., thereby minimizing damage to the body. The surgeon then performs the necessary procedure through the retractor tube using specially designed tools and equipment.

A problem with known retractors used in minimally invasive surgery is that the distal end profile or configuration of the device is fixed. A typical tubular retractor has a circular or elliptical transverse cross-section with the distal end lying in the plane perpendicular or slanted relative to the longitudinal axis. Other tubular distractors may have non-planar ends of varying configurations, such as having a spatula-like extension. Spreading retractors likewise have varying end configurations. Because the distal end configurations of the devices are fixed, the devices often fail to prevent creep or herniation of tissue at or around the distal end of the device, and this tissue creep can interfere with the necessary physical or visual access. This is particularly true when the distal end of the retractor device is positioned adjacent or near a bone, such as a vertebra for example, that does not have a planar or smooth outer contour, or where the retractor device is disposed at a non-perpendicular angle to the bone. In these circumstances it often becomes necessary for the surgeon to cut away the interfering tissue, thereby creating additional tissue damage that needs to heal and increasing the possibility of detrimental results such as bleeding, increased pain, infection and the like.

Some retractors of the spreadable blade type provide shim members that are mounted in interior channels disposed in each of the blades. The shim can be extended beyond the distal end of the blade by sliding the shim relative to the blade. The shortcomings of this solution to the problem of tissue creep is that the location of the shims are determined by the location of the blades after they have been positioned and spread. Thus, the surgeon cannot address the problem of tissue creep that occurs between the blades.

SUMMARY

In accordance with the disclosure, systems, instruments and techniques are provided for enhancing visualization through a retractor during a surgical procedure, particularly a spinal surgery.

In an exemplary embodiment, a surgical retractor extension clip system includes a surgical retractor; an extension clip having a blade that is one of planar and radiused around a long axis, and a mounting means for releasable engagement with the a deployment instrument and includes at least one compression engagement feature which is in some embodiments a compression hook that opposes a compression recess for engagement with a surgical retractor, and a deployment instrument having an handle and an elongate body that is one of curved, bayonetted and straight and proximally and distally oriented engagement features for releasable engagement with the extension clip. The instrument can be actuated by flexion along its axis to direct locking engagement of the extension clip mounting means with the surgical retractor. The system is adapted for engagement of the extension clip with the surgical retractor to mount the extension clip in a locked position for extension of the blade toward or outside of the distal end of the surgical retractor at its distal end.

In use, when fixed to the surgical retractor, at least a portion of the extension clip blade is positioned to contact soft tissue adjacent the distal end of the surgical retractor and thereby minimize tissue creep into the field of the surgical retractor. In some examples, the surgical retractor has an elongate body. In some specific examples, the surgical retractor has a generally cylindrical or ellipsoid elongate body defining a lumen between its proximal and distal ends and in some possible embodiments comprising one or more slot disposed through the elongate body toward the distal end. In some examples, the instrument is adapted for use with a surgical retractor that has a shape that is selected from generally cylindrical with a contiguous solid wall, generally cylindrical with a wall comprising in some possible embodiments one or more slots, generally cylindrical with a wall comprising two vertically adjacent slots, blade shaped having a planar or radiused configuration.

Also provided is a suction/irrigation assembly for engagement with a surgical retractor, the assembly having proximal and distal ends with a proximal grip for engaging the retractor, particularly a tubular retractor, and including an elongate tube contoured to extend on a first end toward a distal end of the retractor and to attach at the proximal end via a port lock to a fluid conduit. the assembly proximal grip includes opposing upper and lower flanges with extensions that form at least one receiver for engagement with a retractor handle.

Other embodiments of extension clips and assemblies for engagement with retractors are provided as shown in the drawings and description.

BRIEF DESCRIPTION OF THE DRAWINGS

Features and advantages of the general inventive concepts will become apparent from the following description made with reference to the accompanying drawings, including drawings represented herein in the attached set of figures, of which the following is a brief description.

Figure 1:
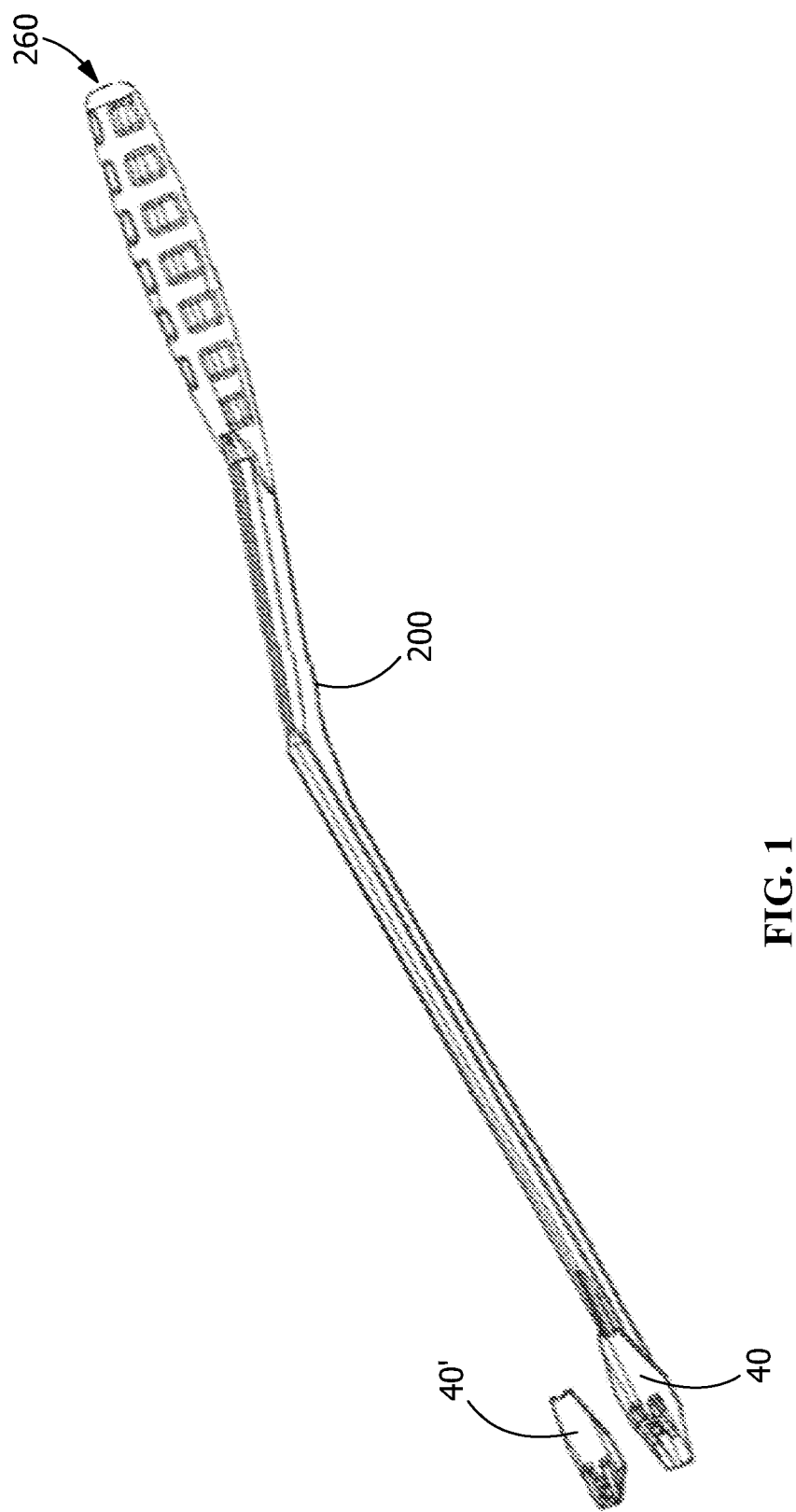
FIG. 1 shows two embodiments of extension clip components and a deployment instrument component of a retractor extension clip system, according to the disclosure.

The following Reference Numeral Key describes various features as shown in the drawings and relating to the various embodiments as set forth in the description and claims:

| | |
|---|---|
| 40 | Extension Clip |
| 41 | Mounting Means |
| 42 | Mounting Recess |
| 43 | Compression Hook |
| 44 | Opposing Locking Flanges |
| 45 | Tool Engagement Aperture |
| 46 | Distal Blade |
| 47 | Distal Edge |
| 48 | Front |
| 49 | Back |
| 00 | Compression Recess |
| 100 | Retractor |
| 102 | Lumen |
| 106 | Proximal End |
| 108 | Distal End |
| 110 | Tubular Body |
| 500 | Suction/Irrigation Assembly |
| 510 | Proximal End |
| 520 | Distal End |
| 530 | Proximal Grip |
| 540 | Tube Distal Tip |
| 550 | Elongate Tube |
| 560 | Port Lock |
| 570 | Grip Lower Flange Extension |
| 580 | Grip Upper Flange Extension |
| 590 | Grip Receiver |
| 200 | Deployment Instrument |
| 210 | Handle |
| 220 | Elongate Body |
| 230 | Bayonetted Neck |
| 240 | Mounting Guide |
| 244 | Flange |
| 250 | Clip Mounting Pin |
| 260 | Proximal End |
| 280 | Distal End |
| 50 | Extension Clip |
| 51 | Mounting Means |
| 52 | Proximal Hook Retainer |
| 53 | Distal Hook |
| 54 | Adjustment Locking Stop |
| 55 | Distal Aperture |
| 56 | Distal Blade |
| 57 | Distal Edge |
| 58 | Front |
| 59 | Back |
| 60 | Extension Clip |
| 62 | Proximal Retaining Flange |
| 63 | Distal Hook |
| 64 | Body |
| 66 | Distal Blade |
| 70 | Clamp |
| 71 | Extension Securement |
| 72 | Locking Stop Engagement Interference Member |
| 73 | Tab Actuator |
| 74 | Retractor Engagement Groove |
| 78 | Clamp Top |
| 79 | Clamp Bottom |
| 80 | Elongate Retainer |
| 81 | Mounting Means |
| 82 | Proximal Hook Retainer |
| 83 | Distal Hook |
| 84 | Adjustment Locking Stop |
| 85 | Proximal Securement Flange |
| 89 | Dimension Indicia |
| 90 | Suction/Irrigation Assembly |
| 92 | Proximal Tube |
| 94 | Distal Tube |
| 96 | Retainer Support |
| 98 | Retainer Securement |
| 99 | Retainer Locking Stop Engagement Interference Member |
| 300 | Retractor |
| 302 | Lumen |
| 306 | Proximal End |
| 308 | Distal End |
| 310 | Tubular Body |
| 320 | Slot |
| 400 | Deployment Instrument |
| 410 | Handle |

-continued

| | |
|---|---|
| 420 | Elongate Body |
| 430 | Bayonetted Neck |
| 440 | Proximal Hook |
| 450 | Clip Mounting Pin |
| 460 | Proximal End |
| 480 | Distal End |

DESCRIPTION

The invention addresses, among other issues, tissue creep, particularly with respect to retractors used in spinal surgical procedures, for example but not limited to TLIF, among others, by providing a retractor device for minimally invasive surgery that incorporates extensions in the form of blades that may be selectively attached within or adjacent or to the end of a tubular shaped retractor, and also are suitable for attachment to other instruments that would benefit from extensions that can contact and retract tissue. The extensions are generally clipped to the tubular retractor.

Figure 2:
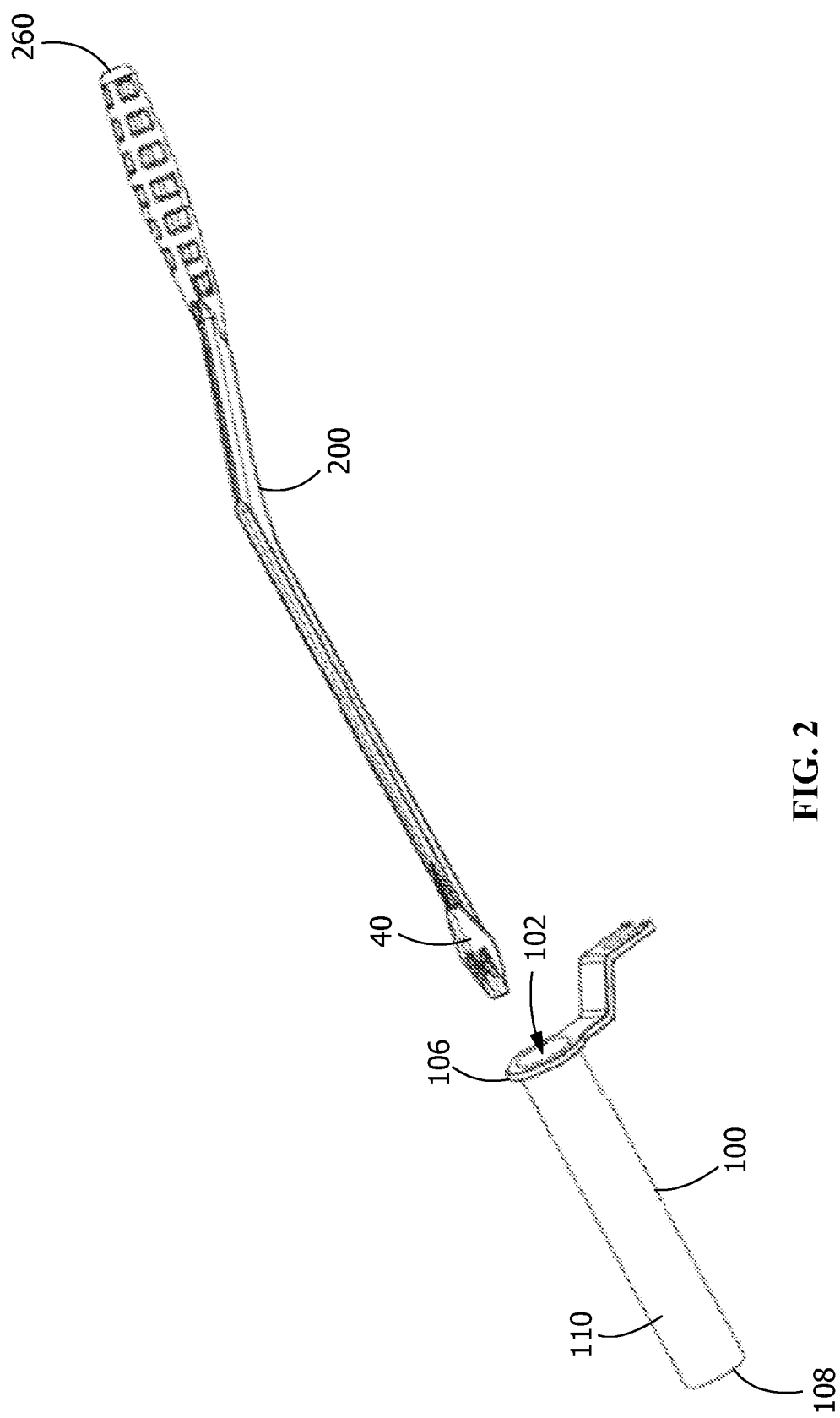
FIG. 2 shows a retractor extension clip system including extension clip and deployment instrument components as shown in FIG. 1 and a retractor.

As shown in the drawings in FIG. 1-16, various components are provided that in various combinations provide systems for adding functionality to surgical retractors. With reference specifically to FIG. 1-9, an embodiment of a retractor extension clip system is shown which in use enables the provision of selective extension of a retractor into a surgical site to urge soft tissue and other material out of the surgical field. According to the embodiment, the extension clips are affixed by compressive force to the retractor, the tips being formed of a polymer or metal that is suitable to provide flexion along a long axis of the clip and at the attachment hook to allow secure fixation to the retractor. Referring now to FIG. 2, a representative embodiment of a retractor extension clip system is shown, which includes (i) a retractor 100 having an elongated tubular body 110, a proximal end 106 and a distal end 108 and a lumen 102 defined therebetween through the tubular body 110, and in some possible embodiments at least one slot 104 positioned on the body at a point between a proximal and distal end; (ii) an extension clip 40 having a distal blade 46, and a mounting means 41 for releasable engagement with a retractor 100, and (iii) a deployment instrument for actuating the extension clip 40 into engagement with the retractor 100.

Figure 3:
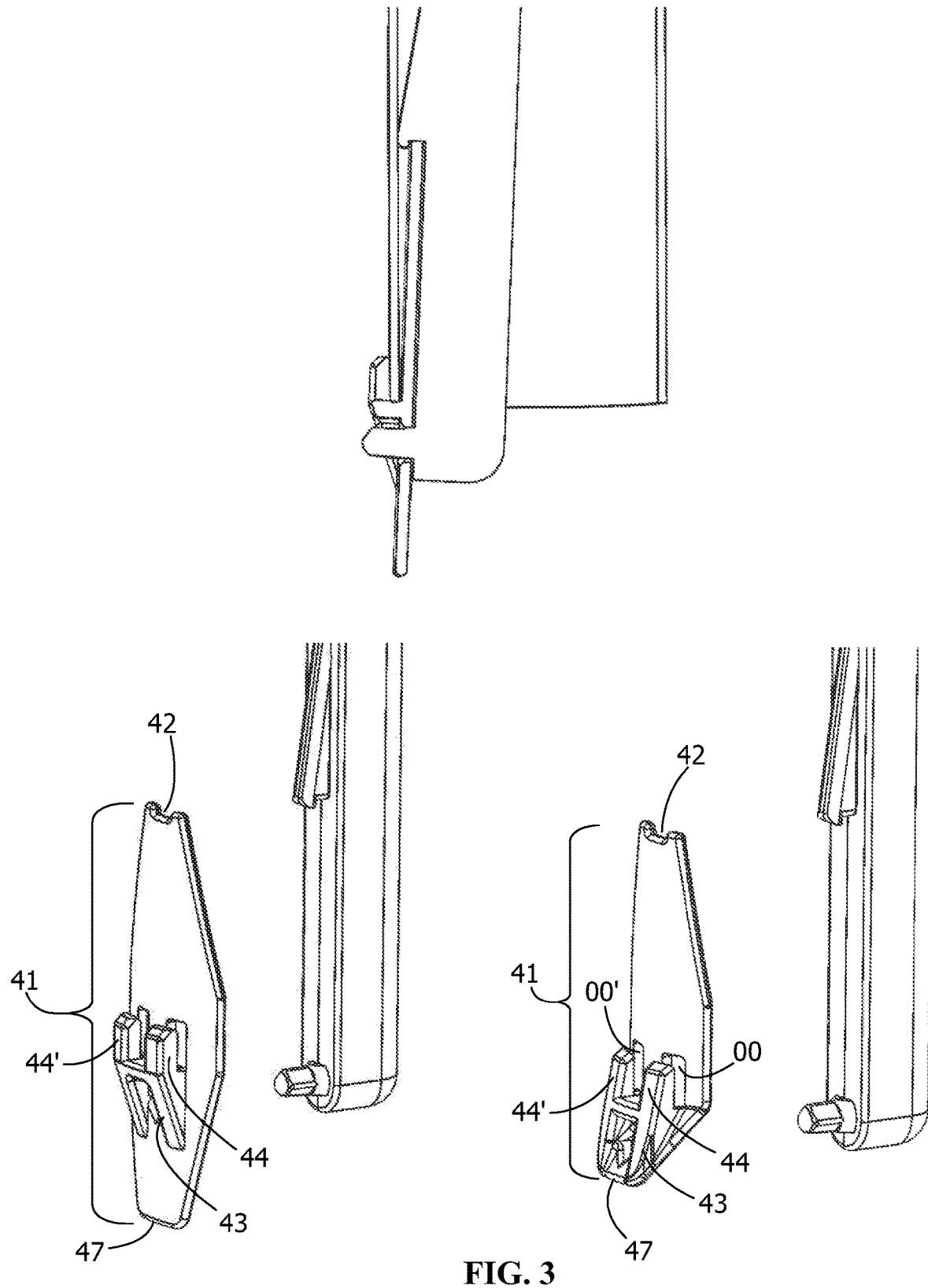
FIG. 3 shows three alternate views of the interaction of the mounting means of an extension clip and a deployment instrument as shown in FIG. 1.

Referring now to FIG. 3, the extension clip 40 is releasably engageable by compressive locking engagement at the distal end 308 of the retractor 300. The extension clip 40 includes a distal blade 46, a mounting means 41 that includes at the proximal end a mounting recess 42 and adjacent its distal edge 47 a compression hook 43, and front and back sides 48, 49. In accordance with the various embodiments, at least the compression hook 43 comprises a distal locking flange that is adapted for snap fitting with one of the end of or a slot of a retractor, the retractor being either planar or tubular. In some embodiments, more than one hook comprises a distal flange.

Figure 6:
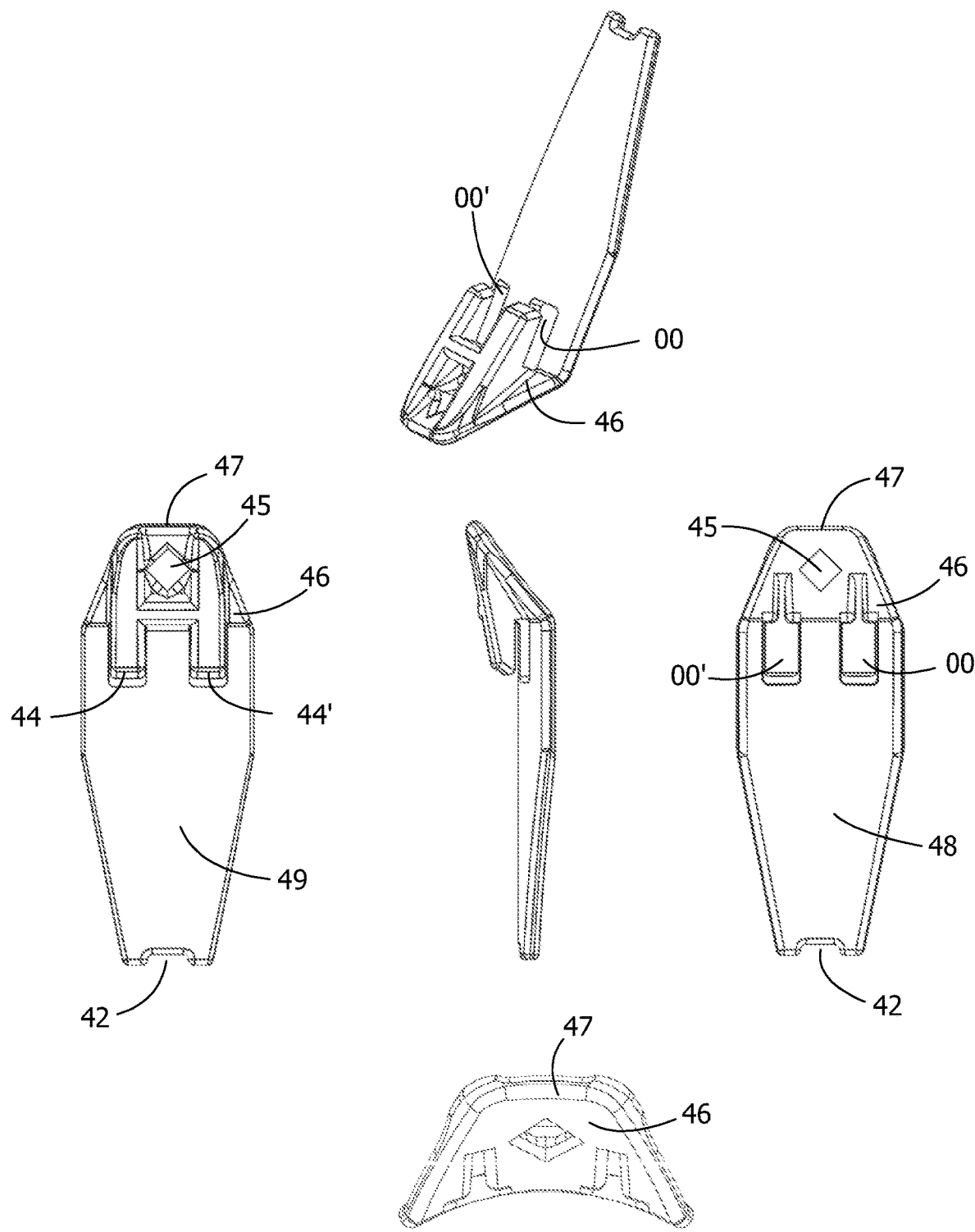
FIG. 6 shows alternate perspective, front, back, side, and end views of the embodiment of an extension clip as shown in FIG. 1.
Figure 7:
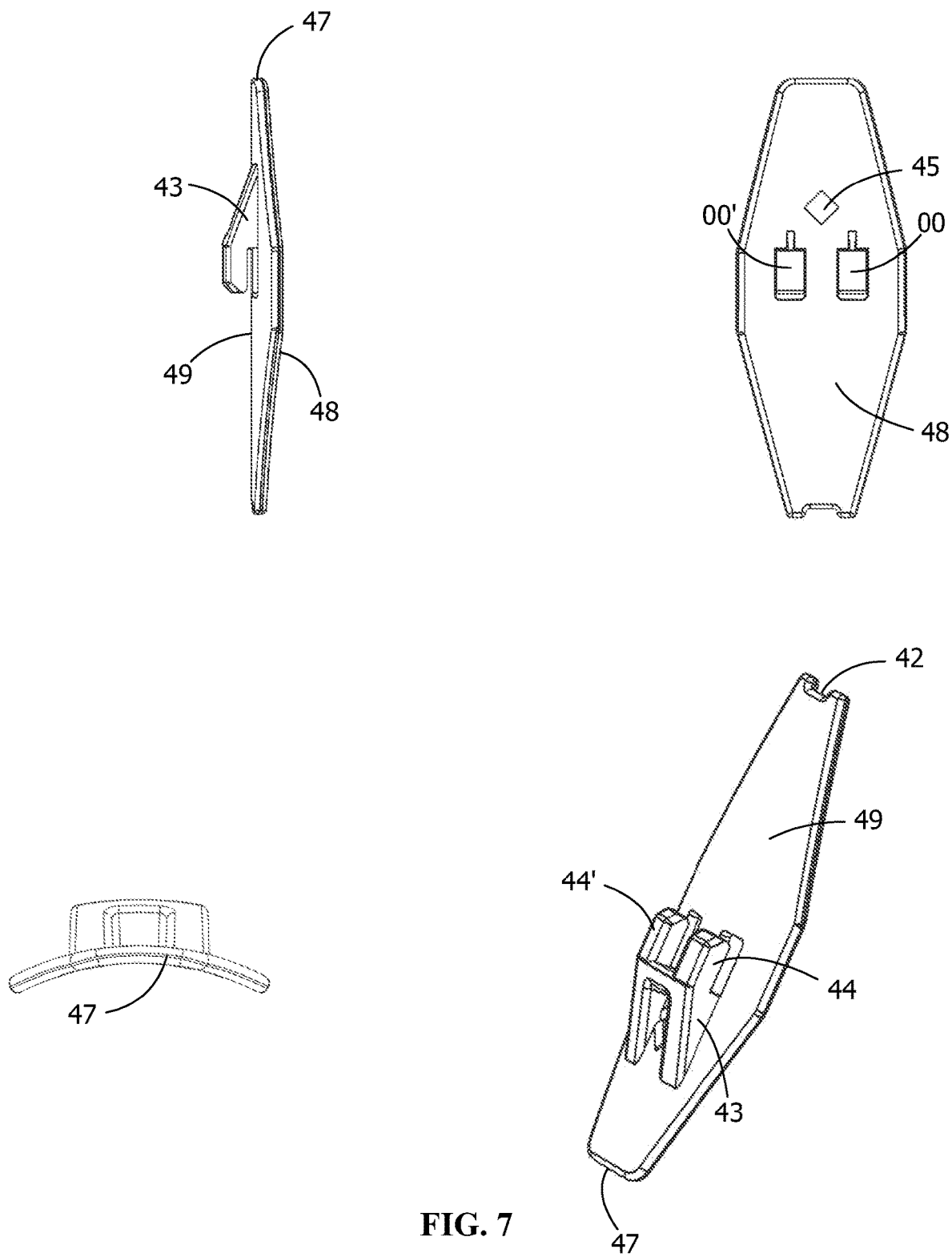
FIG. 7 shows alternate perspective, front, back, side, and end views of another embodiment of an extension clip as shown in FIG. 1.

As depicted, the extension clip 40 is adapted such that the front 48 side is oriented away from a contact surface of the retractor 100. With regard to the specific embodiment shown in FIG. 2, the front 48 side is oriented toward the lumen 102 of the retractor 100, and the back side 49 is adapted to contact a wall of the retractor 100. In some embodiments, the extension clip 40 has an overall flat planar shape. In other embodiments, as depicted in the drawings, the extension clip 40 is radiused around its long axis between proximal and distal ends and thus has a curvature around its long axis wherein in various embodiments this radius matches a radius of the retractor, for example but not limited to a tubular retractor as shown in the drawings, or a blade type retractor (not shown). Extension clips according to the disclosure may be generally straight along their long axis or may include a deflected or beveled tip, as shown in the alternate embodiments depicted in FIG. 1. Thus, in some embodiments the distal blade 46 is straight along the long axis, as depicted in FIG. 7, while in other embodiments, the distal blade 46 is deflected from the elongate axis, the deflection toward the back 49 side, as shown in FIG. 6. It will be appreciated that the angulation of deflection may be varied from between 0 to 90 degrees off the long axis.

The system is adapted for engagement of the retractor extension clip 40 in a fixed, non-moving, position for extension of the distal blade 46 toward or outside of the distal end 108 of the retractor 100, whereby when at least a portion of the distal blade 46 extends outside the distal end 108 of the retractor 100, it is positioned to contact soft tissue and thereby minimizes or precludes tissue creep into the distal end 108 of the retractor 100. The inventive design provides for fixed and releasable engagement of an extension clip 40 with a retractor 100 such that the forces that would be directed on the extension clip 40 will tend to retain the fixation of the clip 40 to the retractor 100 rather than to urge it out of engagement. Thus, in the various embodiments, the extension clips 40 are retained on the retractor 100 by a mounting means 41 for releasable engagement with a deployment instrument 200 and include at least one compression engagement feature which is in some embodiments a compression hook 43 that opposes a compression recess 00 for engagement with a surgical retractor 100. As described below, the primary direction of force against the extension clips 40 would be expected from the sides and the bottom, which forces tend to reinforce the fixation of the extension clip 40.

Figure 10:
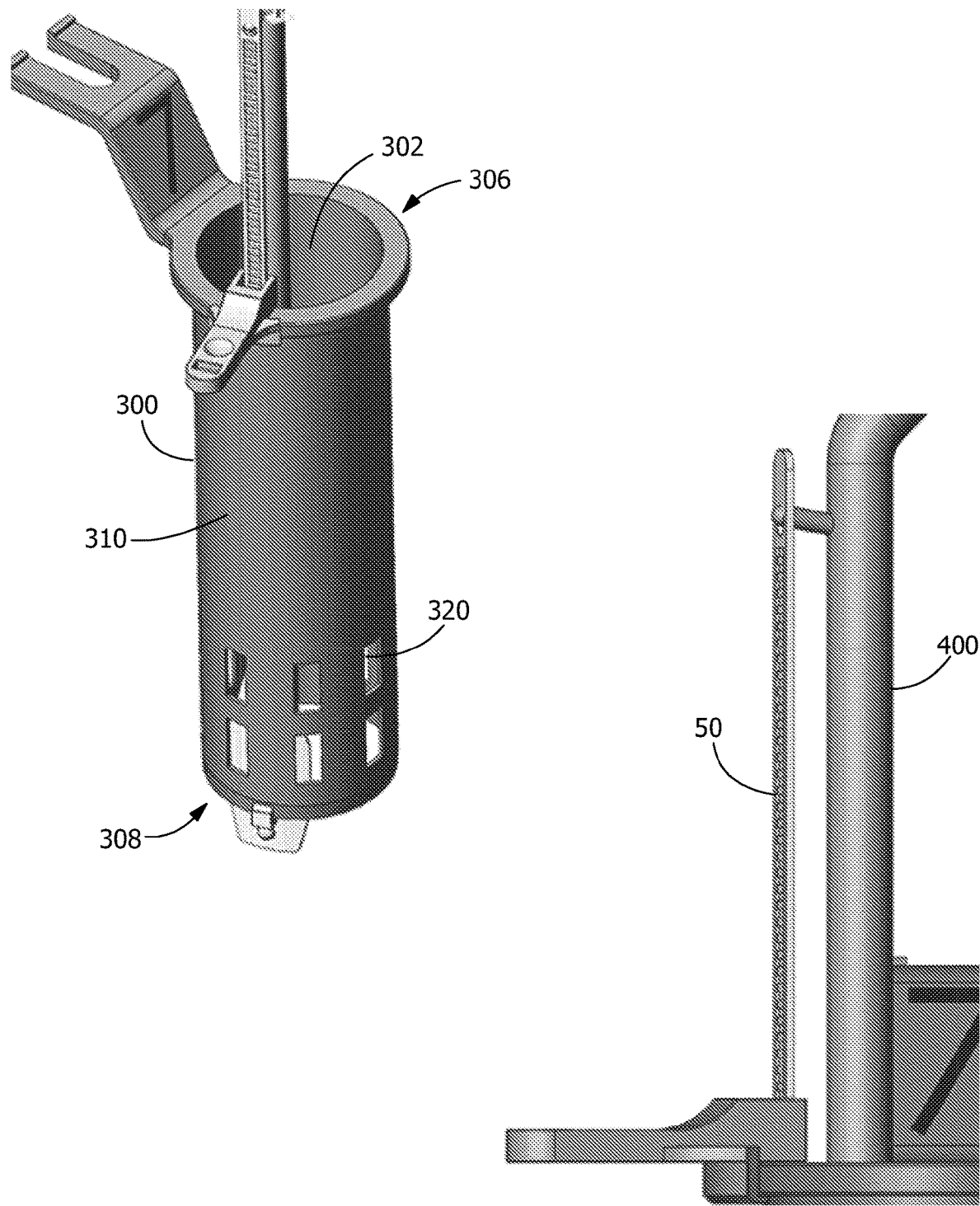
FIG. 10 shows in the upper left panel an alternate embodiment of a retractor extension clip system according to the disclosure, depicting a representative embodiment of a retractor and a first embodiment of an alternate extension clip engaged with the retractor via a proximal clamp, and in the lower right panel a close up view of the proximal end of the retractor depicting the proximal engagement of the alternate extension clip via the clamp.

Of course, it will be appreciated that the tubular body 110 that is depicted in the drawings is merely representative, and other similar retractors 100 may be used in its place, for instance those that are formed of a unitary tubular or other shaped body, and those that may be assembled by the arrangement of an array of two or more panels, paddles or extension clips 40 to form a port or access to a surgical site. Thus, while the depicted embodiments of the inventive devices in this disclosure are shown in the context of a tubular retractor, it will be understood that the inventive devices may be used with other retractor devices as well as curved and planar retractors and similar instruments that are adapted with one or more slots, for example as shown in FIG. 10, for engagement with the inventive extension devices and suitable for insertion into a surgical space to retract tissue.

Figure 4:
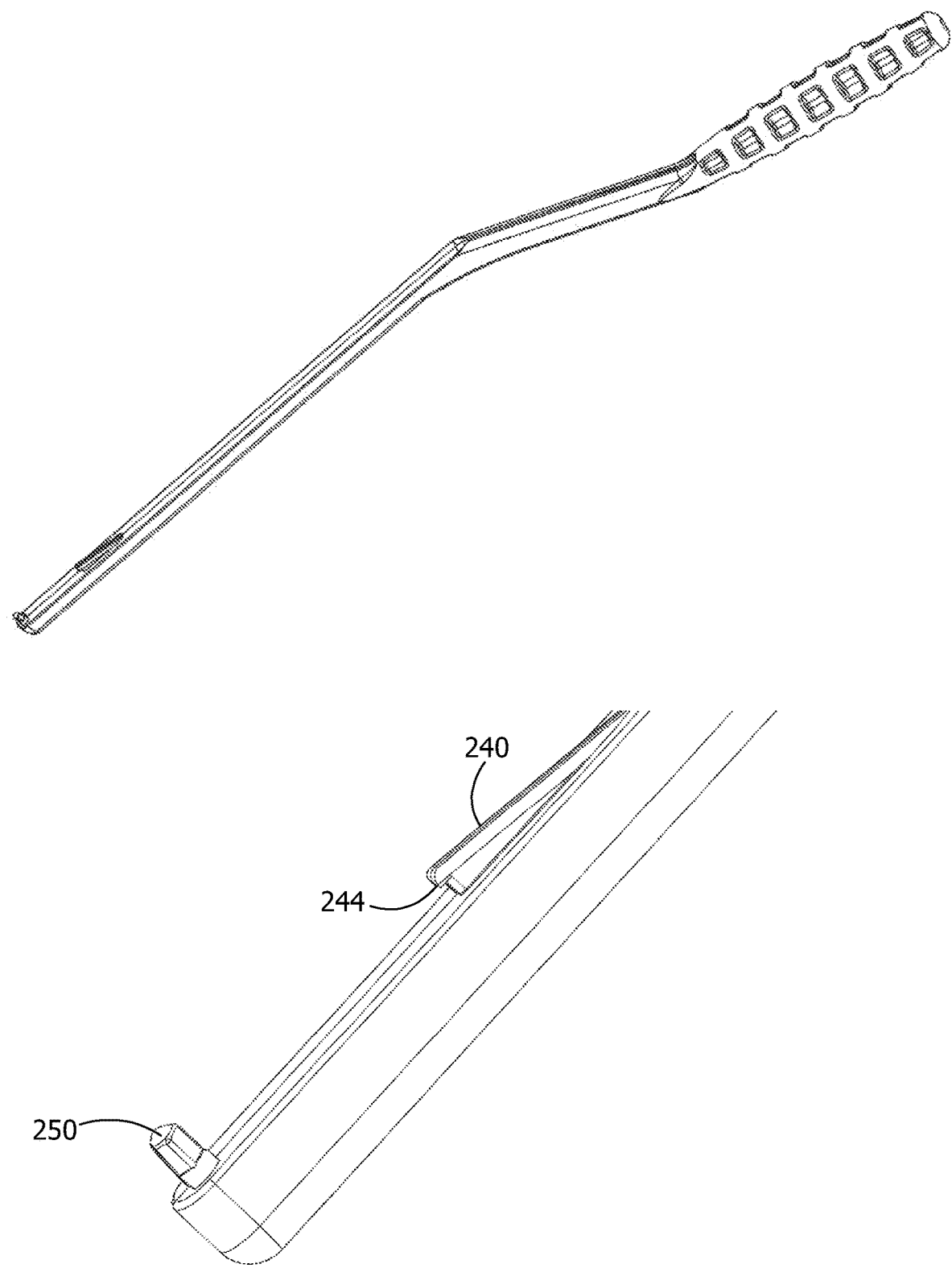
FIG. 4 shows alternate full perspective and distal end close up views of a representative embodiment of a deployment instrument as shown in FIG. 1.
Figure 5:
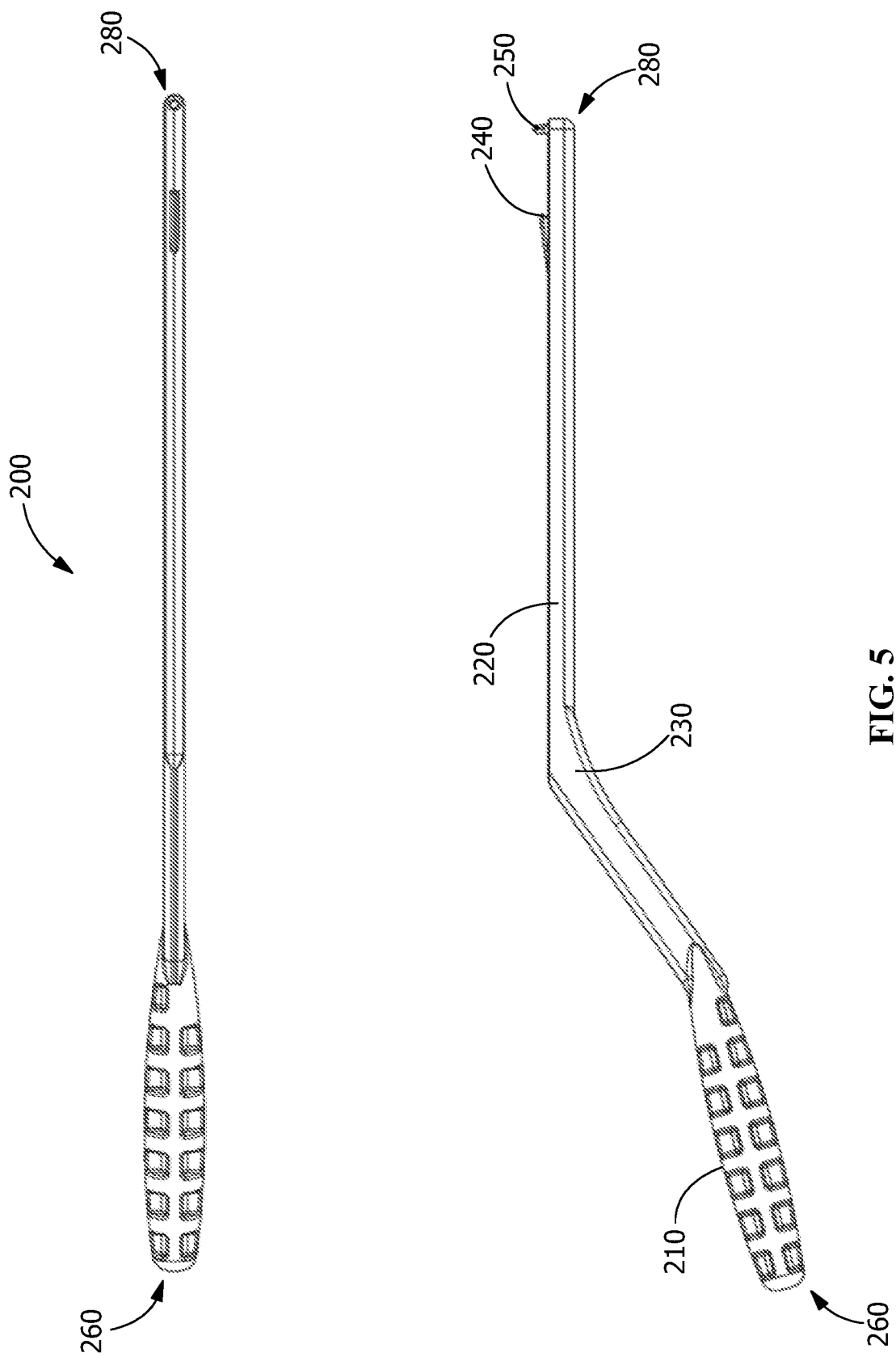
FIG. 5 shows alternate top and perspective views of a deployment instrument as shown in FIG. 1.

Referring now to FIG. 4 and FIG. 5, the system includes a deployment instrument 200 having an handle 210 and an elongate body 220 between proximal 270 and distal ends 280 that is one of curved, bayonetted and straight. As shown in the drawings, the depicted embodiment of the instrument 200 includes a bayoneted neck 230. It will be appreciated that in other embodiments, the instrument 200 may be straight and lacks a bayoneted neck, or may include another feature such as a curve or a bend with greater or lesser angulation than as depicted. In the various embodiments according to the disclosure, the instrument 200 includes proximally and distally oriented engagement features, as shown including a proximally oriented mounting guide 240 that includes a flange 244, and a distally oriented clip mounting pin 250, each of the engagement features adapted for engagement with corresponding features in the extension clip 40, the features inter-engaging for releasable engagement between the instrument 200 and the extension clip 40, as shown for example in FIG. 3. The instrument can be actuated by flexion along its axis such that when engaged with an extension clip 40, the clip 40 can be contacted with a wall of a retractor whereby the compression hook 43 is slid into contact with an edge of the retractor 100, and the clip 40 is flexed such that opposing locking flanges 44, 44' of the compression hook 43 flex to allow the hook to fully seat on the retractor edge, the compression recess 00 allowing enhanced flexion. The engagement between the mounting guide 240 and the tool mounting recess 42 maintains flexion of the clip 40 until flexion of the instrument 200 is relaxed, thereby releasing the clip 40 from engagement with the instrument 200 whereby the compression hook 43 compresses back side 49 of the clip 40 against and into fixed engagement with the retractor edge.

As is described herein above, a key aspect of the engagement features of the instant invention is that the forces required to unlock the engagement features of the extension clip, and in some embodiments comprising a slot, must be directed towards the distal end of the retractor tube, whereas the direction of the forces against the extension clips are either lateral or upward. In use, the counter forces on the retractor tips come primarily from (i) lateral forces directed against the front of the distal blades due to contact with surgical tools, (ii) lateral forces against the back of the distal blades due to pressure exerted by the soft tissue, and (iii) proximally directed vertical forces due to pressure exerted by the soft tissue against the back side 49 of the clip blade 46. The direction of these forces would not operate to disengage the locked clips.

It is contemplated that the invention may be provided to surgeons or other users in the form of a kit, such kit comprising a retractor with a solid wall or a retractor having at least one slot and a plurality of extension clips of varying shapes and sizes, a deployment instrument, and other optional components.

In some embodiments, extension clips may be deployed partially or wholly within the retractor and may be used for retention of one or more insertable instruments. In some examples these would include irrigation, suction, electro/neuromonitoring, fiber optic lighting, camera or other instruments to facilitate the surgical procedure. Thus, in addition to extension clips for clearance of soft tissue from a retractor, also provided herein are adaptations for retractor tubes to facilitate the securement of instruments within the tube. In some embodiments, the adaptations include one or more flexible clips that are adapted to be secured to the walls of the tube specifically for retaining in place one or more instruments. In use, the instrument, such as a tubular light, camera, neuro-monitoring cable, or the like is inserted in the tube into the surgical field and is clipped to the tube by engagement of the adapted extension clips within in the slots.

Figure 8:
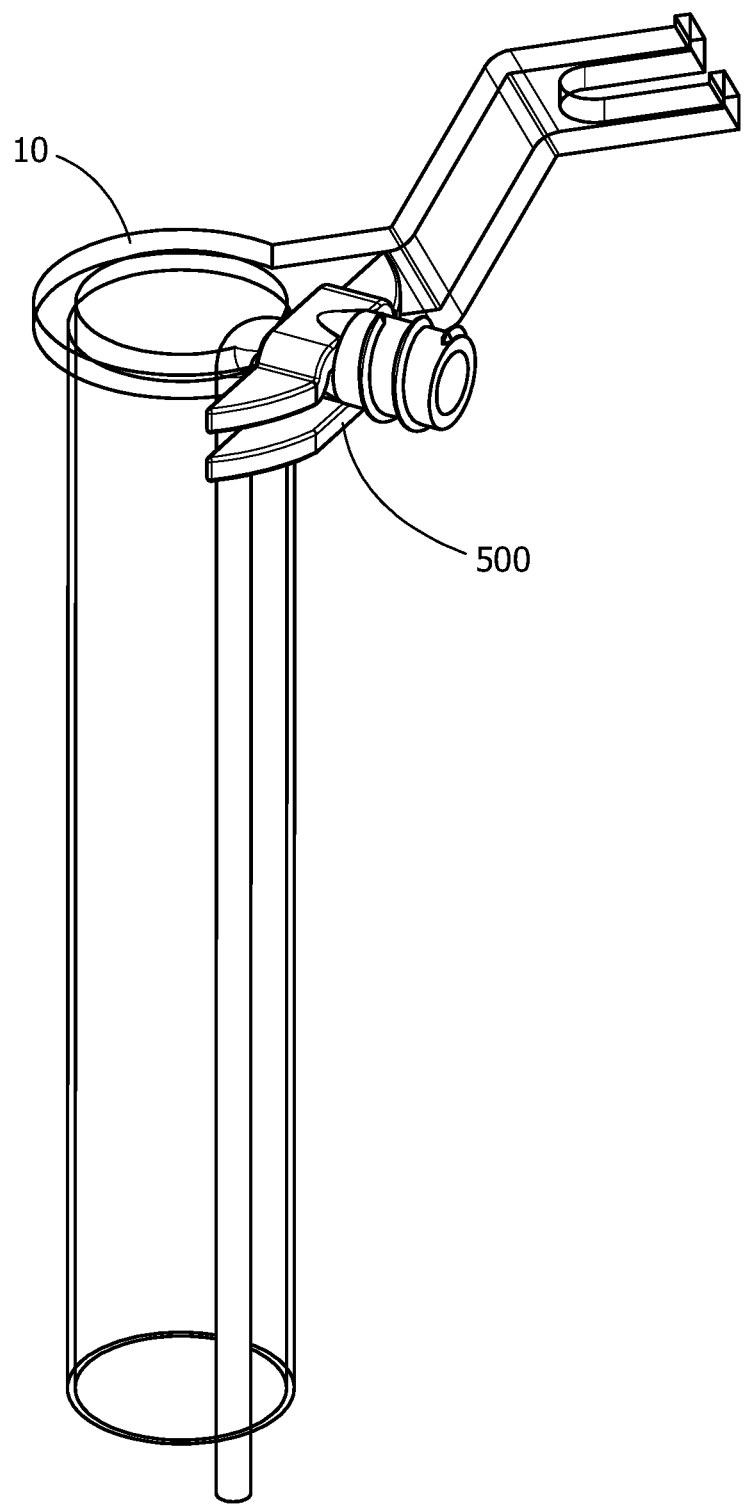
FIG. 8 shows a perspective view of a suction/irrigation assembly affixed to a tubular retractor that is shown as transparent.
Figure 9:
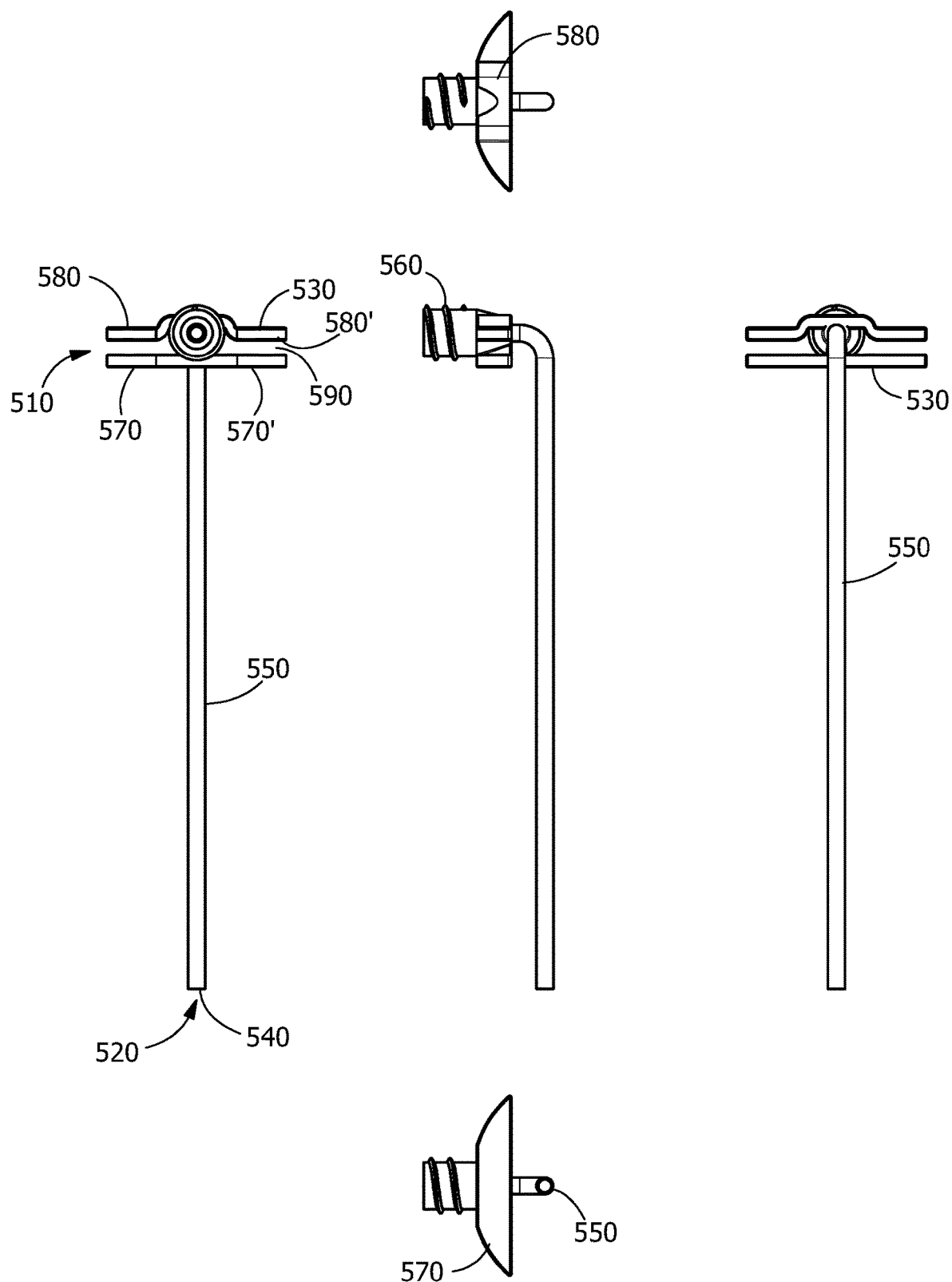
FIG. 9 shows alternate front, back, side, top and bottom views of the suction/irrigation assembly as shown in FIG. 8.

Referring now to FIG. 8 and FIG. 9 is a suction/irrigation assembly 500 is provided for engagement with a surgical retractor 100, the assembly 500 having proximal 510 and distal 520 ends with a proximal grip 530 for engaging the retractor 100 via a structure such as a handle as depicted in the drawings, particularly a tubular retractor 100, and including an elongate tube 550 contoured to extend on a the distal end 520 toward a distal end of the retractor and to attach at the proximal end 510 via a port lock 560 to a fluid conduit (not shown). the assembly 500 proximal grip 530 includes opposing upper 580 and lower 570 flanges with extensions 580, 580' and 570, 570' that form at least one receiver 590 for engagement with a retractor handle. As depicted, the opposing flanges 570, 580 are generally winged shaped and form mirror image receivers 590, 590' that allow the assembly 500 to be slid to one side or the other of a retractor 100 feature such as a handle to allow greatest range for attachment of the assembly 500. Of course, other attachment means, including selected from those shown herein, may be employed to grip the assembly to a retractor.

In use, an array of the extension clips is provided with retractors adapted for engagement with at least one more of the array of extension clips. Upon accessing the surgical field in a patient, a retractor and clip combination are selected, and the retractor is inserted into position in the field according to standard protocol. Thereafter, the one or more suitably dimensioned extension clips are selected, and serially, each is engaged with the appropriate insertion instrument. The engaged instrument and clip are passed into the lumen of the retractor body. As determined by the surgeon, the distal end of the clip may be maneuvered first into contact with the soft tissue below/adjacent the distal end of the retractor so as to initially displace the tissue away from the distal lumen opening. While retaining contact with the displaced soft tissue, the surgeon extension clip mounting means is guided into initial alignment with the retractor which may in some possible embodiments include a slot or slots and the tool is thereafter manipulated to actuate insertion and engagement of the mounting means with the retractor tube and in some possible embodiments a slot/slots. Multiple extension clips may be deployed, including clips with varied configurations as selected by the surgeon to address the anatomical variations within the soft tissue adjacent the retractor. After engagement and locking is achieved, the insertion tool is disengaged and withdrawn from the retractor lumen. In some instances, the tool may be reinserted into the lumen to adjust the position of or remove the extension clip. In some examples the instrument may be used with another instrument to achieve unlocking of the extension clip prior to extraction from the retractor end and/or slot. Upon completion of the surgical procedure, one or more of the extension clips may be detached and removed prior to removal of the retractor, or they may be left in place and removed with the retractor member.

Embodiments of the present invention are suitable for use, in some examples, in a posterior or transforaminal approach for spinal surgery, and may be adapted for uses in other spinal surgical orientations and other surgical sites within the body.

Adjustable Extension Clips and Retainers

In an alternate embodiment, the retractor extension clip systems include features that enable fixation of clips at the proximal end of a retractor, such as but not limited to a tubular retractor. Referring again to the drawings, according to the depicted embodiments as shown in FIG. 10-FIG. 16, the clip extensions are joined to a retractor surface or wall by utilization of a vertically adjustable tab mechanism, as described below.

Figure 12:
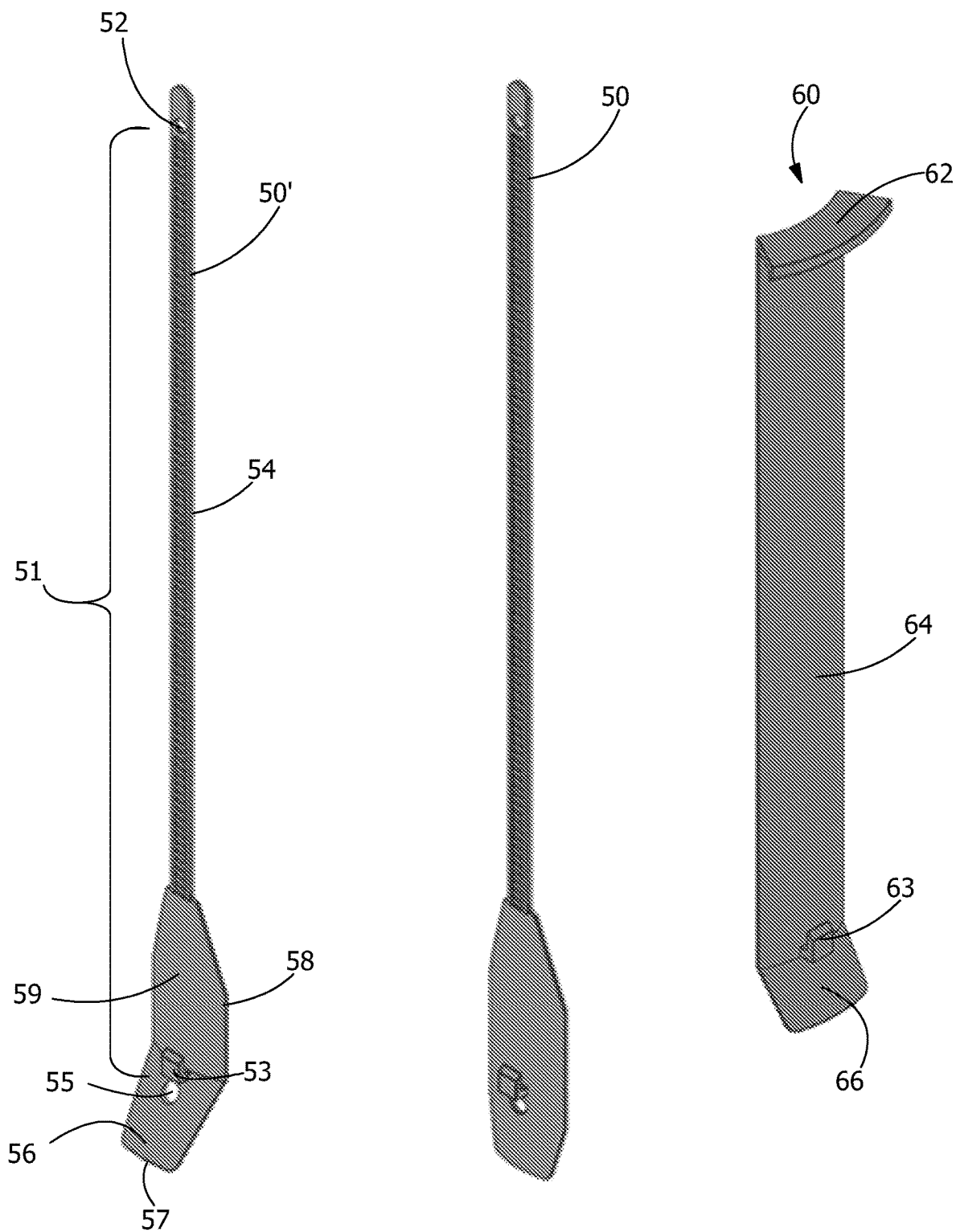
FIG. 12 shows perspective views of three alternate extension clips.

In various embodiments, as shown in the drawings, retractor clips and elongate retainers for securing tools and instruments, such as irrigation, suction, illumination, and electrical instruments, for example, are provided as elongate extensions. As shown in FIG. 10, a retractor clip 50 includes a distal blade that includes a distal hook, and an elongate vertically adjustable tab that includes an elongate tab extension having at least one adjustment locking stop 54 and a proximal clamp 70, the clamp 70 and the adjustment locking stop 54 of the elongate tab extension of the vertically adjustable tab are engageable for adjustable and releasable engagement. The retractor clips 50 are affixed along an elongate wall, for example, an elongate wall of a retractor 300 having an elongated tubular main body 310 with a proximal 306 and a distal end 308 and an inner lumen 302. FIG. 12 shows two alternate embodiments of the retractor clip 50, one having an angled and the other a straight blade 56 that terminates in a blade edge 57. FIG. 12 also shows an alternate embodiment of an extension clip 60 that is engageable with proximal and distal ends of a retractor tube via a proximal retaining flange 62 and a distal hook 63 at respective ends of a body 64. The clip 60 includes a distal blade 66.

Alternate views of the system are shown in each of FIG. 10-FIG. 13. As shown in FIG. 10, the retractor clips 50 are adapted for engagement in a fixed, non-moving, position for extension of the blade 56 toward or outside of the distal end 308 of the retractor 300. referring again to FIG. 10 and FIG. 13, the extension clip 50 includes a mounting means 51, a proximal hook retainer 52, a distal hook 53, and adjustment locking stop 54, a distal aperture 55, a distal blade 56, a distal edge 57, and a front 58 and a back 59.

Figure 13:
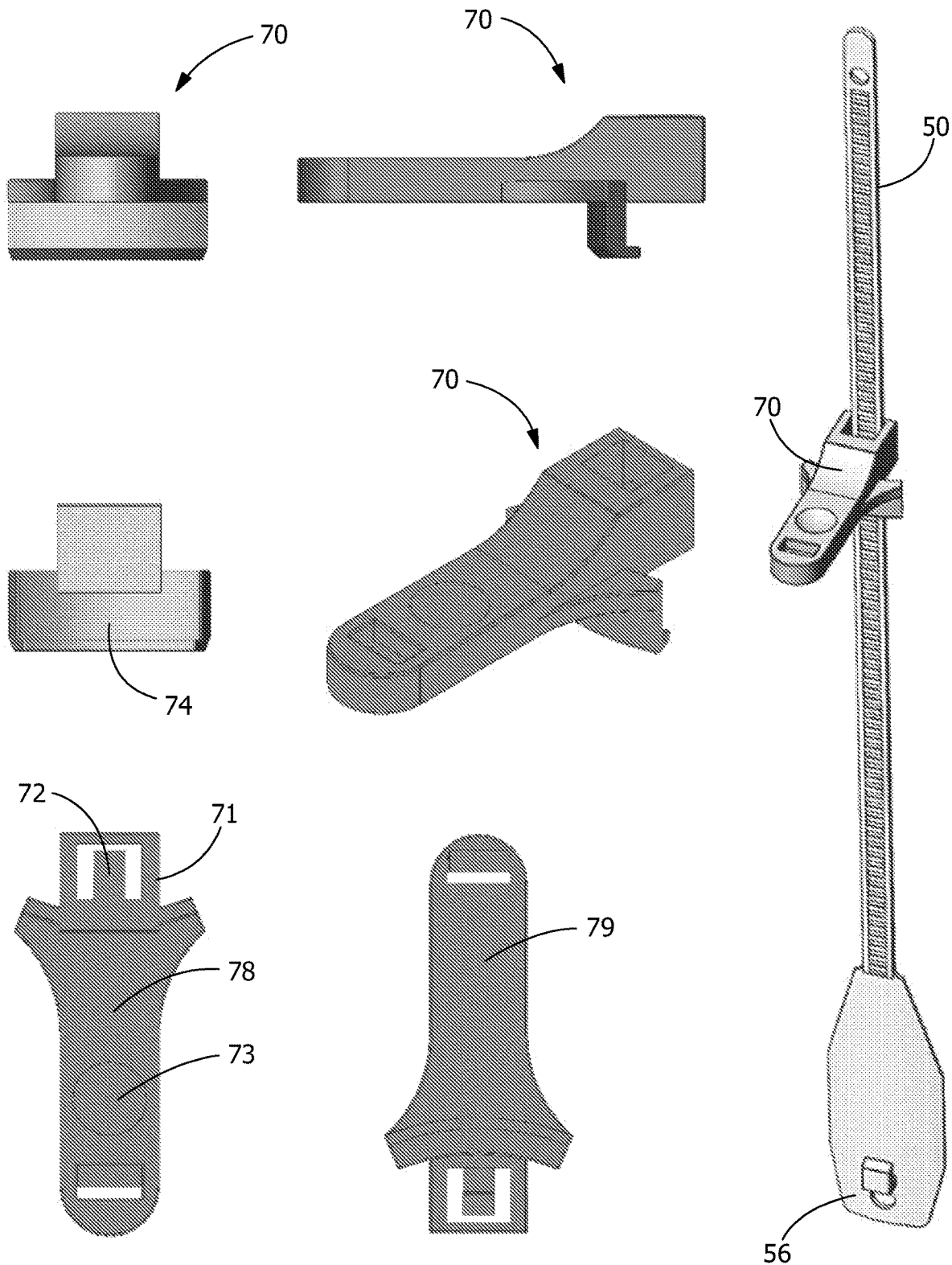
FIG. 13 shows alternate views of an embodiment of an extension clip clamp in back, side, front, back perspective, top and bottom views, and as attached to a representative extension clip in perspective view according to the embodiment shown in FIG. 10.

Referring to FIG. 10 and FIG. 13, the vertically adjustable tab clamp 70 engages with the proximal edge of the retractor body and the blade hook 53 is affixed to the distal end of the retractor body to achieve vertically locked fixation of the retractor extension to the retractor. The clamp 70 includes an extension securement 71 for receiving a proximal end of the retractor clip 50, a locking stop engagement interference member 72 for engagement with the adjustment locking stop 54, a tab actuator 73 for engagement of the locking stop 54 with the interference member 72, a retractor engagement groove 74 for affixing to an proximal edge of a retractor, particularly a cylindrical retractor as shown in the drawings, the clamp including a clamp top 78 and a clamp bottom 79. In use, the retractor is inserted in contact with tissue, when at least a portion of the extension blade 56 extends outside the distal end of the retractor body, the blade 56 it is positioned to contact soft tissue and thereby minimize or preclude tissue creep into the distal end 308 of the retractor 300.

Figure 11:
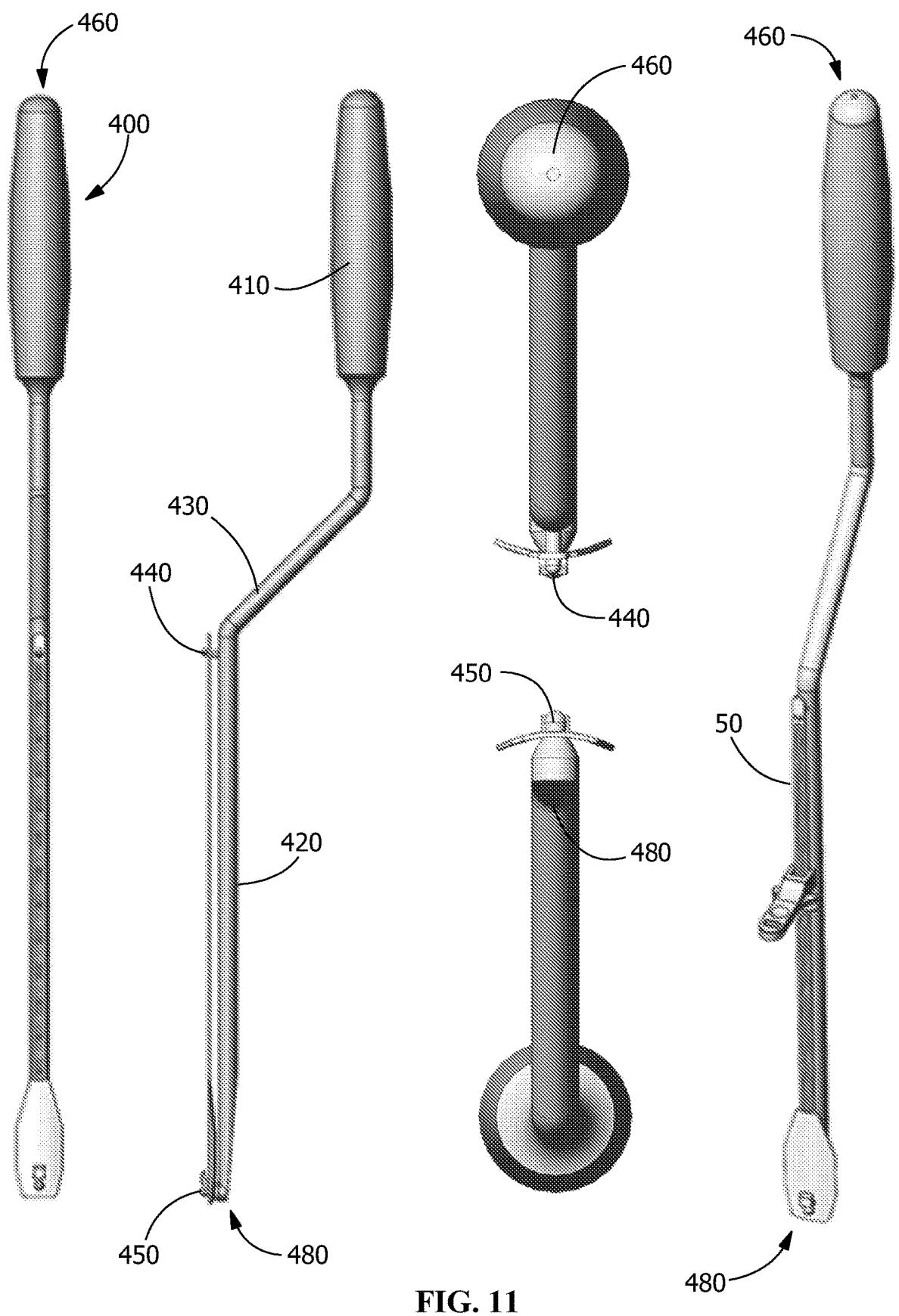
FIG. 11 shows an alternate embodiment of a deployment instrument according to the disclosure, in front, side, top, bottom and perspective views.

Referring now to FIG. 11, an alternate embodiment of a deployment instrument 400 is shown. As described above, the instrument engages with a clip 50 for deployment in a retractor and includes a handle 410, an elongate body 420, a bayonetted neck 430, a proximal hook 440, a clip mounting pin 450 all defined between a proximal end 460 and a distal end 480. The instrument 400 is adapted to engage with the mounting means 51 of the clip 50, wherein the proximal hook retainer 52 engages with the proximal hook 440 and the distal hook 53 engages with the clip mounting pin 450 to direct the clip 50 into contact with a retractor wall, whereupon the clamp 70 is affixed to the clip 50 and actuated for achieving locking engagement therebetween.

In some embodiments, the tubular body 310 of the retractor 300 is adapted with at least one slot 320 or one or more a circumferential rings of slots allowing flexibility in the position of placement of the extension clips and allowing for multiple extension clips to be positioned around the circumference of the retractor 100. It will be appreciated that the shape of the slots 320 may be varied, as well as their distribution and orientation around the circumference, as well as their proximal to distal positioning. Thus, in some embodiments, the slots 320 may be positioned at any location between the proximal 306 and distal 308 ends. In some embodiments, only one slot 320 may be included. And in other embodiments, two or more circumferential rows of slots 320 may be present. Thus, it will be appreciated that in various embodiments, the tubes may be adapted with slots 320 at more than one position along the length from the proximal 306 to distal 308 ends of the tubes, and that the shapes, sizes, number and distribution of the slots 320 may vary to accommodate varying sized extension clips and to support instruments that may be affixed to an extension clip along all or a portion of the length of the tubular body 310. More generally, it will be appreciated that in the context of other retractors, such as single and multi-bladed retractors that may be straight or radiused, one or more slots could likewise be used for placement of one or more extension clips.

Figure 14:
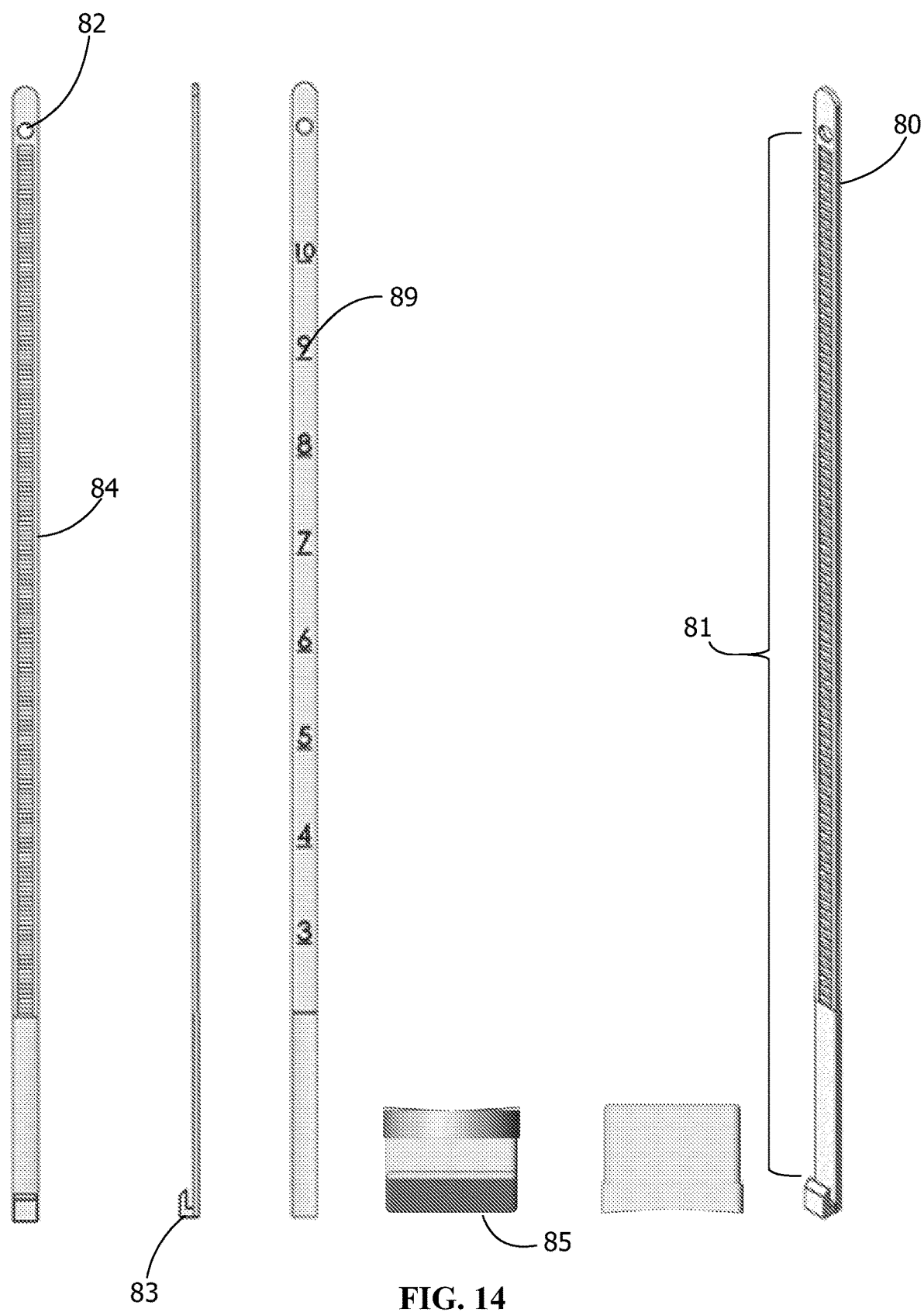
FIG. 14 shows alternate views of another embodiment of an extension clip and clamp in front, side, back, and perspective views of the clip and front and back views of the clamp, the mechanism used for affixing an irrigation and/or suction assembly to a retractor.
Figure 15:
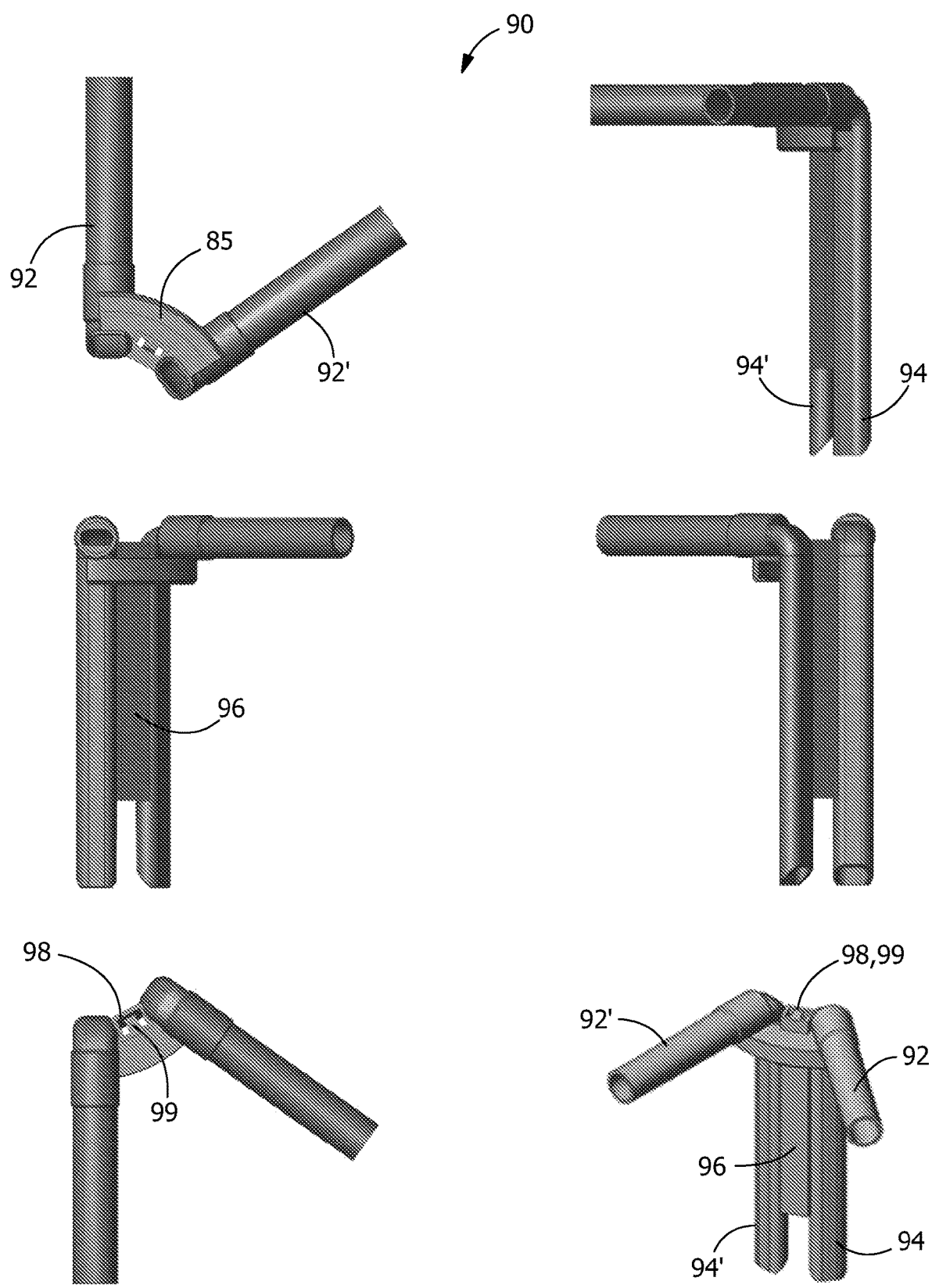
FIG. 15 shows alternate views of an alternate embodiment of an irrigation and/or suction assembly in top, outer side, inner side, back, bottom and front perspective views.
Figure 16:
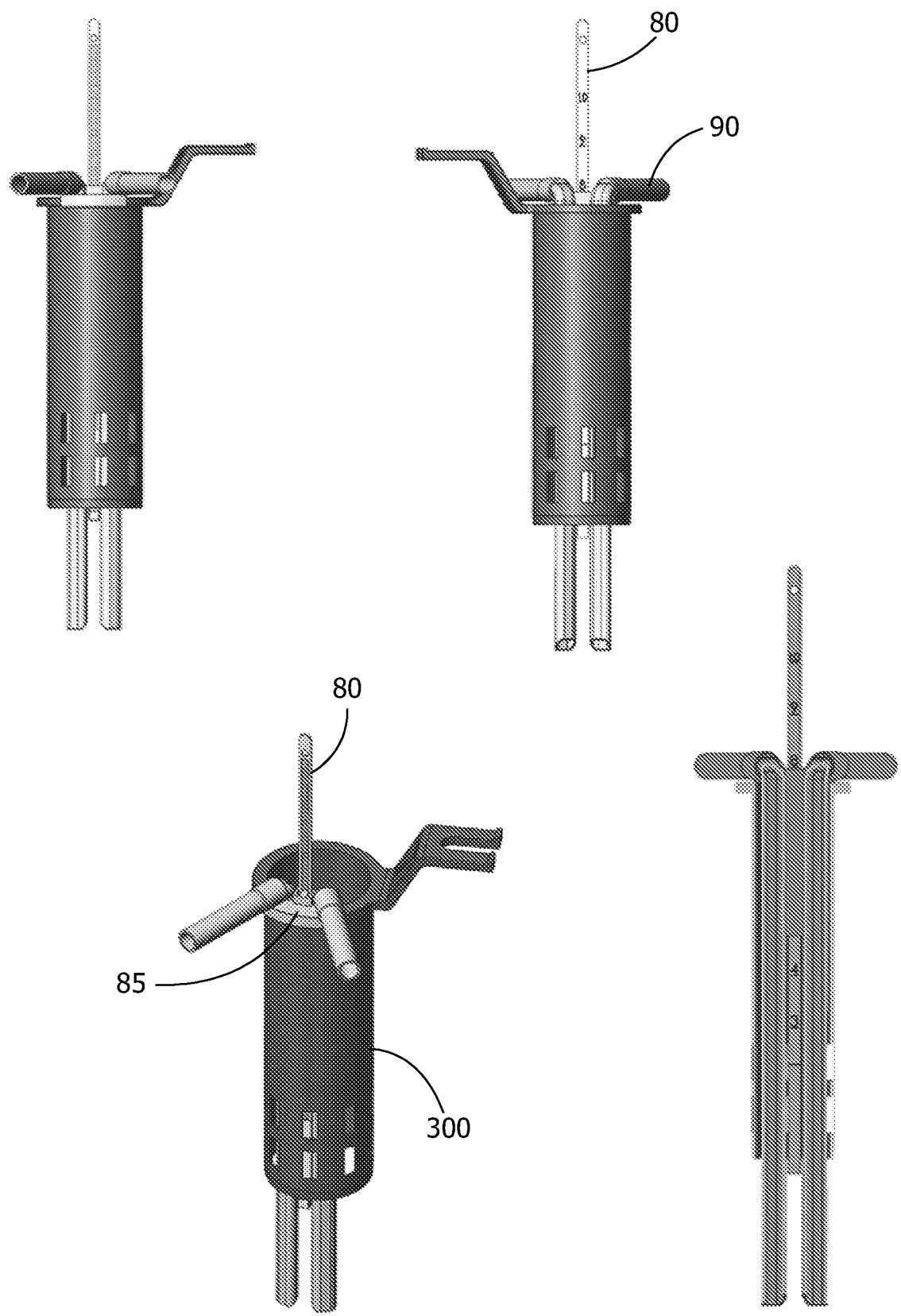
FIG. 16 shows alternate views of an irrigation and/or suction assembly as shown in FIG. 15 affixed to a tubular retractor with an extension clip and clamp according to FIG. 14, including front, top perspective, back and cross sectional back views.

Also provided and as shown in FIG. 14-16 are attachment components and tube arrays 90 for provision of suction and irrigation, which are attachable using the vertically adjustable tab mechanism of the illustrated elongate retainer 80. Referring again to FIG. 14, the depicted elongate retainer 80, includes a mounting means 81, a proximal hook retainer 82, a distal hook 83, an adjustment locking stop 84, a proximal securement flange 85, and dimension indicia 89. The retainer 80 may be used to secure instruments to a retractor, for example as shown in FIG. 16, to mount a Suction/Irrigation Assembly 90. As shown, the assembly 90 includes a Proximal Tube 92, a Distal Tube 94, a Retainer Support 96 for contacting a retainer 80, a Retainer Securement 98 for receiving a retainer 80 and a Retainer Locking Stop Engagement Interference Member 99 for engagement with an adjustment locking stop 84.

Embodiments of the present invention are suitable for use, in some examples, in a posterior or transforaminal approach for spinal surgery, and may be adapted for uses in other spinal surgical orientations and other surgical sites within the body.

Installing Instruments Using Vertically Adjustable Tab System

Slide the vertically adjustable tab clamp 70 onto the top of the retractor tube, for example in some uses, no more than 20 mm (¾") from the top of the vertically adjustable tab. The vertically adjustable tab clamp 70 shown here is farther than 20 mm. The size is merely representative and may be varied in any manner to meet the dimensions of the tube or other instrument to which it is attached.

Push the vertically adjustable tab lower hole onto the bayonet instrument so the vertically adjustable tab lies against the main body of the instrument.

Once the tissue to be retracted is identified, move the instrument and vertically adjustable tab to the retraction location, and engage the vertically adjustable tab hook on the bottom edge of the tube and pull up until the hook bottoms out on the edge.

Slide the vertically adjustable tab hole onto the bayonet instrument so the vertically adjustable tab lies against the main body of the instrument.

Pivot the instrument out of the bottom vertically adjustable tab hole.

Slide the instrument out of the top vertically adjustable tab hole.

Tighten the clamp against the top edge of the tube.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

The general inventive concepts may be embodied in different forms and should not be construed as limited to the embodiments set forth herein. Rather, these embodiments are provided so that this disclosure will be thorough and complete, and will fully convey the scope of the general inventive concepts to those skilled in the art.

As used herein, the singular forms "a," "an," and "the" are intended to include the plural forms as well, unless the context clearly indicates otherwise. The term "proximal" as used in connection with any object refers to the portion of the object that is closest to the operator of the object (or some other stated reference point), and the term "distal" refers to the portion of the object that is farthest from the operator of the object (or some other stated reference point). The term "operator" means and refers to any professional or paraprofessional who delivers clinical care to a medical patient, particularly in connection with the delivery of care.

Anatomical references as used herein are intended to have the standard meaning for such terms as understood in the medical community. For example, the application may include reference to the following terms: "cephalad," "cranial" and "superior" indicate a direction toward the head, and the terms "caudad" and "inferior" indicate a direction toward the feet. Likewise, the terms "dorsal" and "posterior" indicate a direction toward the back, and the terms "ventral" and "anterior" indicate a direction toward the front. And the term "lateral" indicates a direction toward a side of the patient. The term "medial" indicates a direction toward the mid line of the patient, and away from the side, the term "ipsalateral" indicates a direction toward a side that is proximal to the operator or the object being referenced, and the term "contralateral" indicates a direction toward a side that is distal to the operator or the object being referenced. And, more specifically with respect to the directional movement of an implant according to the methods of the disclosure, sideways refers to the general direction of movement within the disc space between the endplates from the position of the inserted instruments toward one or the other of the contralateral and ipsalateral portions of the disc space. In the case of a TLIF procedure, such sideways motion will generally be in a medial direction relative to the disc space. Though in other types of surgical access, particularly within the spine, sideways movement may be either medial or lateral relative to the disc space, and in other surgical contexts sideways is away from the initial position of the implant. Further, with respect to the movement of an implant by action of the surgical instruments, the movement may also be rotational, wherein the action of the instruments directs the implant sideways and also in a rotational or pivotal motion. More generally, any and all terms providing spatial references to anatomical features shall have meaning that is customary in the art.

Unless otherwise indicated, all numbers expressing quantities, properties, and so forth as used in the specification, drawings and claims are to be understood as being modified in all instances by the term "about." Accordingly, unless otherwise indicated, the numerical properties set forth in the specification and claims are approximations that may vary depending on the suitable properties desired in embodiments of the present invention. Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements.

References to visualization using radiography as may be described in the exemplary techniques herein are merely representative of the options for the operator to visualize the surgical field and the patient in one of many available modalities. It will be understood by one of ordinary skill in the art that alternate devices and alternate modalities of visualization may be employed depending on the availability in the operating room, the preferences of the operator and other factors relating to exposure limits. While confirmation of instrument placement in the course of the technique is appropriate, the frequency and timing relative to the sequence of steps in the technique may be varied and the description herein is not intended to be limiting. Accordingly, more or fewer images, from more or fewer perspectives, may be collected.

One of ordinary skill will appreciate that references to positions in the body are merely representative for a particular surgical approach. Further, all references herein are made in the context of the representative images shown in the drawings. Fewer or additional instruments, including generic instruments, may be used according to the preference of the operator. Moreover, references herein to specific instruments are not intended to be limiting in terms of the options for use of other instruments where generic options are available, or according to the preference of the operator.

While the disclosed embodiments have been described and depicted in the drawings in the context of the human spine, it should be understood by one of ordinary skill that all or various aspects of the embodiments hereof may be used in in connection with other species and within any species on other parts of the body where deep access within the tissue is desirable.

While various inventive aspects, concepts and features of the general inventive concepts are described and illustrated herein in the context of various exemplary embodiments, these various aspects, concepts and features may be used in many alternative embodiments, either individually or in various combinations and sub-combinations thereof. Unless expressly excluded herein all such combinations and sub-combinations are intended to be within the scope of the general inventive concepts. Still further, while various alternative embodiments as to the various aspects, concepts and features of the inventions (such as alternative materials, structures, configurations, methods, devices and components, alternatives as to form, fit and function, and so on) may be described herein, such descriptions are not intended to be a complete or exhaustive list of available alternative embodiments, whether presently known or later developed.

Those skilled in the art may readily adopt one or more of the inventive aspects, concepts and features into additional embodiments and uses within the scope of the general inventive concepts, even if such embodiments are not expressly disclosed herein. Additionally, even though some features, concepts and aspects of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated.

Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated.

The invention claimed is:

1. A retractor extension clip deployment system, comprising:
   an extension clip having proximal and distal ends; and
   a deployment instrument,
   the extension clip comprising at the distal end at least one hook for engagement with a distal end of a surgical retractor, and a proximal elongate tab comprising a proximally positioned aperture and configured in length to extend to and be affixed to a proximal edge of the retractor,
   the deployment instrument comprising a handle, and an elongate body comprising a proximally oriented engagement pin for releasable engagement with the proximally positioned aperture of the extension clip,
   wherein the deployment instrument is adapted for actuating and directing engagement of the at least one hook at the distal end of the extension clip with the distal end of the surgical retractor and extension of the proximal end of the extension clip outside a proximal end of the surgical retractor.

2. The retractor extension clip deployment system according to claim 1, the extension clip comprising a distal blade that extends below the at least one hook, and at least one distally oriented aperture, and the deployment instrument comprising a distally oriented engagement pin for releasable engagement with the distally oriented aperture of the extension clip, wherein the extension clip is engageable with the surgical retractor for extension of the distal blade of the extension clip outside the distal end of the surgical retractor.

3. The retractor extension clip deployment system according to claim 2, the extension clip further comprising a proximal clamp that is actuatable to fixedly engage the proximal end of the extension clip to the proximal end of the surgical retractor.

4. The retractor extension clip deployment system according to claim 3, wherein the proximal clamp is releasably engageable with the proximal end of the extension clip.

5. The retractor extension clip deployment system according to claim 2, wherein the proximally and distally oriented pins of the deployment instrument aligned with one another along the axis of the deployment instrument.

6. The retractor extension clip deployment system according to claim 2, wherein the distal blade is one of planar and radiused around a long axis of the distal blade.

7. The extension clip deployment system according to claim 2, wherein the distal blade includes a distally oriented portion that is angled.

8. The retractor extension clip deployment system according to claim 2, wherein the extension clip further comprises a compression recess through the extension clip at the distal end adjacent the at least one hook to accommodate flexion of the at least one hook.

9. The retractor extension clip deployment system according to claim 2, wherein the at least one hook comprises a pair of locking flanges.

10. The retractor extension clip deployment system according to claim 2, wherein the extension clip is adapted for engagement with a surgical retractor that has a generally cylindrical or ellipsoid elongate body defining a lumen between its proximal and distal ends.

11. The retractor extension clip deployment system according to claim 2, wherein the extension clip is adapted for engagement with a surgical retractor comprising at least one slot disposed through the elongate body toward a distal end.

12. The surgical retractor system according to claim 1, wherein the deployment instrument includes a neck that is distal to the handle and is bayoneted.

13. The retractor extension clip deployment system according to claim 1, further comprising a fluid transport assembly adapted to be affixed to the surgical retractor, the fluid transport assembly comprising at a proximal end a proximal flange for releasably engaging the proximal edge of the surgical retractor, the proximal flange of the fluid transport assembly positioned between two elongate tubes, each elongate tube having proximal and distal ends and each elongate tube attached to the fluid transport assembly at the proximal end adjacent to the proximal flange, wherein each elongate tube is contoured near the proximal end with a radius that directs each elongate tube to extend distally to provide a fluid conduit.

14. The retractor extension clip deployment system according to claim 13, wherein the fluid transport assembly is engageable with an extension clip for securing the fluid transport assembly from the proximal to the distal end of the surgical retractor.

15. The retractor extension clip deployment system according to claim 1, further comprising a surgical retractor having an elongate body, a proximal end and a distal end, the elongate body having a contour along an axis from proximal to distal that is generally cylindrical.

16. A method for deploying a retractor extension into engagement with a surgical retractor, the method comprising:
   (i) providing a retractor extension clip having a proximal end comprising a proximally oriented elongate tab, and a distal end comprising a hook and a distally oriented blade, the retractor extension clip adapted to attach to a surgical retractor having proximal and distal ends, a proximal edge and a proximal handle that is oriented at an angle relative to a distal elongate wall, wherein the retractor extension clip has at least one adjustment locking stop;
   (ii) passing the retractor extension clip into a lumen defined by the elongate wall of the surgical retractor when the surgical retractor is positioned in a surgical field adjacent spinal vertebra and associated soft tissue;
   (iii) maneuvering the distal end of the retractor extension clip into contact with the soft tissue that is adjacent the distal end of the surgical retractor to displace the soft tissue away from the lumen defined by the elongate wall of the surgical retractor;
   (iv) affixing the distal hook of the retractor extension to the distal end of the surgical retractor, whereby at least a portion of the distal blade of the retractor extension extends outside the distal end of the retractor;
   (v) affixing a clamp at the proximal end of the elongate tab into fixed engagement with the proximal edge of the surgical retractor, whereby the proximal end of the elongate tab and the distal hook are engaged respectively with the proximal and distal ends of the surgical retractor to provide tension along the retractor extension clip and secure fixation of the retractor extension clip to the surgical retractor, wherein the clamp has a locking stop engagement, and the clamp and the at least one adjustment locking stop are engageable for adjustable and releasable engagement.

17. The method for deploying a retractor extension into engagement with a surgical retractor according to claim 16, wherein the elongate tab comprises a plurality of adjustment locking stops for adjustable and releasable engagement therebetween.

18. A retractor tool deployment system, comprising: a fluid transport assembly adapted to be affixed to a surgical retractor having a proximal edge and a proximal handle that is oriented at an angle relative to a distal elongate wall, the fluid transport assembly having proximal and distal ends and comprising at its proximal end a proximal flange for releasably engaging the proximal edge of the surgical retractor, the proximal flange of the fluid transport assembly positioned between two elongate tubes, each elongate tube having proximal and distal ends and each elongate tube attached to the fluid transport assembly at its proximal end adjacent to the proximal flange, wherein each elongate tube is contoured near its proximal end with a radius that directs each elongate tube to extend distally along the distal elongate wall of the surgical retractor to provide a fluid conduit.

19. The retractor tool deployment system according to claim 18, further comprising an extension clip having proximal and distal ends and comprising a proximal elongate tab that is engageable with the proximal end of the fluid transport assembly and a distal hook for engagement with a distal end of the surgical retractor to secure the fluid transport assembly along the distal elongate wall of the surgical retractor.

20. The retractor tool deployment system according to claim 19, further comprising a clamp at the proximal end of the proximal elongate tab.

* * * * *